(12) United States Patent
Asher et al.

(10) Patent No.: US 7,954,360 B2
(45) Date of Patent: Jun. 7, 2011

(54) FIELD MOUNTED ANALYZER WITH A GRAPHICAL USER INTERFACE

(75) Inventors: Jonathan W. Asher, Bartlesville, OK (US); Anthony P. Walker, Bartlesville, OK (US); James Michael Robinson, Bartlesville, OK (US)

(73) Assignee: ABB Inc., Cary, NC (US)

( * ) Notice: Subject to any disclaimer, the term of this patent is extended or adjusted under 35 U.S.C. 154(b) by 801 days.

(21) Appl. No.: 11/925,066

(22) Filed: Oct. 26, 2007

(65) Prior Publication Data

US 2008/0087072 A1   Apr. 17, 2008

Related U.S. Application Data

(62) Division of application No. 11/515,079, filed on Sep. 1, 2006, now Pat. No. 7,743,641.

(60) Provisional application No. 60/713,986, filed on Sep. 2, 2005.

(51) Int. Cl.
*G01N 30/00* (2006.01)
*G01N 30/88* (2006.01)

(52) U.S. Cl. ............ 73/23.36; 73/23.35; 95/82; 96/101

(58) Field of Classification Search .............. 73/23.35, 73/23.36, 23.41, 23.42; 95/82; 96/101, 102, 96/103
See application file for complete search history.

(56) References Cited

U.S. PATENT DOCUMENTS

| | | |
|---|---|---|
| 3,069,894 A | 12/1962 | Claudy |
| 3,070,989 A | 1/1963 | Dueker et al. |
| 3,119,252 A | 1/1964 | Nerheim |
| 3,139,755 A | 7/1964 | Reinecke et al. |
| 3,374,660 A | 3/1968 | McKinney et al. |
| 3,429,176 A | 2/1969 | Topham |
| 3,910,765 A | 10/1975 | Tinklepaugh et al. |
| 4,044,593 A | 8/1977 | Haruki et al. |
| 4,057,755 A | 11/1977 | Piesche |
| 4,088,458 A | 5/1978 | Jourdan |
| 4,735,082 A | 4/1988 | Kolloff |
| 4,854,952 A | 8/1989 | Stepien |
| 4,869,282 A | 9/1989 | Sittler et al. |
| 5,005,399 A | 4/1991 | Holtzclaw et al. |
| 5,105,652 A | 4/1992 | Manfredi et al. |
| 5,151,688 A | 9/1992 | Tanaka et al. |
| 5,231,381 A | 7/1993 | Duwaer |
| 5,255,074 A * | 10/1993 | Kimbell et al. ............... 356/445 |

(Continued)

FOREIGN PATENT DOCUMENTS

DE   10301601   8/2004

(Continued)

OTHER PUBLICATIONS

ABB Inc., TotalFlow Model 8000/8100 BTU/CV Transmitter user manual, Totalflow Products, Bartlesville, Oklahoma 74006 U.S.A.

(Continued)

*Primary Examiner* — Daniel S Larkin
(74) *Attorney, Agent, or Firm* — Paul R. Katterle

(57) ABSTRACT

The present invention is directed to a field-mounted analyzer having a graphical user interface (GUI). The analyzer has a display screen visible from the exterior of the housing. A plurality of magnetically-actuatable switches are mounted behind the display screen. The GUI has a plurality of windows that may be displayed on the display screen. Navigation through the windows is accomplished by activating switches aligned with graphical navigation icons in the windows.

18 Claims, 34 Drawing Sheets

U.S. PATENT DOCUMENTS

| | | | |
|---|---|---|---|
| 5,265,459 A | 11/1993 | Cohen | |
| 5,278,543 A | 1/1994 | Orth et al. | |
| 5,285,064 A | 2/1994 | Willoughby | |
| 5,298,225 A | 3/1994 | Higdon | |
| 5,313,061 A | 5/1994 | Drew et al. | |
| 5,340,543 A | 8/1994 | Annino et al. | |
| 5,369,386 A | 11/1994 | Alden et al. | |
| 5,379,630 A | 1/1995 | Lacey | |
| 5,389,951 A | 2/1995 | Baker | |
| 5,461,204 A | 10/1995 | Makinwa et al. | |
| 5,495,769 A | 3/1996 | Broden et al. | |
| 5,544,276 A | 8/1996 | Loux et al. | |
| 5,587,520 A | 12/1996 | Rhodes | |
| 5,587,559 A | 12/1996 | Fleck et al. | |
| 5,663,488 A | 9/1997 | Wang et al. | |
| 5,746,976 A | 5/1998 | Yamada et al. | |
| 5,750,939 A | 5/1998 | Makinwa et al. | |
| 5,756,878 A | 5/1998 | Muto et al. | |
| 5,764,928 A | 6/1998 | Lanctot | |
| 5,796,347 A | 8/1998 | Zulaski | |
| 5,808,179 A | 9/1998 | Sittler et al. | |
| 5,950,674 A | 9/1999 | Wylie et al. | |
| 5,983,703 A | 11/1999 | Wylie et al. | |
| 6,004,514 A | 12/1999 | Hikosaka et al. | |
| 6,028,699 A | 2/2000 | Fisher | |
| 6,029,499 A | 2/2000 | Sittler et al. | |
| 6,062,095 A | 5/2000 | Mulrooney et al. | |
| 6,102,449 A | 8/2000 | Welsh | |
| 6,365,105 B1 | 4/2002 | Waters et al. | |
| 6,374,860 B2 | 4/2002 | Xu et al. | |
| 6,437,774 B1 * | 8/2002 | Tsuji et al. | 345/173 |
| 6,453,725 B1 | 9/2002 | Dahlgren et al. | |
| 6,510,740 B1 | 1/2003 | Behm et al. | |
| 6,568,244 B2 | 5/2003 | Binz et al. | |
| 6,598,460 B2 | 7/2003 | Muto | |
| 6,701,774 B2 | 3/2004 | Srinivasan et al. | |
| 6,718,817 B1 | 4/2004 | Ko et al. | |
| 6,742,544 B2 | 6/2004 | Bergh et al. | |
| 6,761,056 B2 | 7/2004 | Schram et al. | |
| 6,896,238 B2 | 5/2005 | Wang | |
| 6,910,394 B2 | 6/2005 | Kriel | |
| 7,004,191 B2 | 2/2006 | Shajii et al. | |
| 7,063,302 B2 | 6/2006 | Cordill | |
| 7,120,508 B2 | 10/2006 | Peshkin et al. | |
| 7,134,354 B2 | 11/2006 | Nelson et al. | |
| 7,197,338 B2 * | 3/2007 | Ozawa | 455/566 |
| 7,506,533 B2 | 3/2009 | Bailey et al. | |
| 2005/0100479 A1 | 5/2005 | White et al. | |
| 2006/0210441 A1 | 9/2006 | Schmidt et al. | |
| 2007/0089484 A1 | 4/2007 | Bailey et al. | |
| 2007/0204673 A1 | 9/2007 | Bailey | |
| 2008/0052013 A1 | 2/2008 | Bailey et al. | |
| 2008/0072976 A1 | 3/2008 | Bailey et al. | |
| 2008/0087072 A1 | 4/2008 | Asher et al. | |
| 2008/0092627 A1 | 4/2008 | Hadley et al. | |

FOREIGN PATENT DOCUMENTS

| | | | | |
|---|---|---|---|---|
| JP | 54-159643 | * | 12/1979 | 40/409 |
| WO | WO01/71340 | | 9/2001 | |
| WO | WO2007/028130 | | 3/2007 | |

OTHER PUBLICATIONS

Emerson Process Management, Danalyzer 700 Product Data Sheet, DAN-GC700-DS-1005, Oct. 2005.

Emerson Process Management, Danalyzer 700 Product Data Sheet, DAN-GC700-DS-53/0803, Aug. 2003.

* cited by examiner

Diagnostic Summary

Last Diagnostic Time: 12/18/05

| | | |
|---|---|---|
| Column 1 Pressure | 0.000 | Idle |
| Column 2 Pressure | 0.000 | Idle |
| Oven Temperature | 0.000 | Idle |
| Column 1 Effort | 0.000 | Idle |
| Column 2 Effort | 0.000 | Idle |
| Oven Effort | 0.000 | Idle |
| Stream 1 | Idle | |
| Stream 2 | Idle | |
| Stream 3 | Idle | |
| Stream 4 | Idle | |

BACK

| Alarm | Mode | Stream | Time |
|---|---|---|---|
| Normal | Run | 1 | 115 |

Alarm Log

No Faults: 0   No Alarms: 0
App ID: ???   Alarm No: 0
Seq No: 0   User Code: 0
Date/Time: 12/18/05 12:00:00   Sev: General
Desc: ???   State: Clear Next   Prev   BACK

| Alarm | Mode | Stream | Time |
|---|---|---|---|
| Normal | Run | 1 | 115 |

Next Stream   614

Fig. 31

FIELD MOUNTED ANALYZER WITH A GRAPHICAL USER INTERFACE

CROSS-REFERENCE TO RELATED APPLICATION

This application is a divisional patent application of, and claims priority from, U.S. patent application Ser. No. 11/515,079, filed on Sep. 1, 2006 now U.S. Pat. No.: 7,743,641, which claims the benefit of U.S. Provisional Application No. 60/713,986, filed on Sep. 2, 2005, each of which is hereby incorporated by reference in its entirety.

BACKGROUND OF THE INVENTION

A conventional field-mounted analyzer has a housing enclosing an analytical assembly for measuring one or more process variables. Some of these analyzers have a display mounted to the housing, wherein the display has a single fixed window for displaying a limited amount of information. Other analyzers have a display device that is separate from the housing and includes a keyboard or key pad that permits an operator to navigate through a plurality of different windows.

SUMMARY OF THE INVENTION

In accordance with the present invention, an analyzer is provided for measuring one or more process variables. The analyzer includes a housing adapted for field mounting and a display screen visible from the exterior of the housing. A plurality of magnetically-actuatable switches are mounted behind the display screen. An electronics assembly is disposed in the housing and includes a microprocessor and memory. The microprocessor is connected to the display screen and the magnetically-actuatable switches. A graphical user interface (GUI) software application is stored in the memory and is executable by the microprocessor to display a plurality of windows on the display screen. The windows contain graphical navigation icons and information about the operation of the analyzer, wherein each window contains at least one navigation icon that is associated with another window and is aligned with one of the switches. When the window is displayed and the switch aligned with the navigation icon is activated, the GUI software application displays the other window.

Also provided in accordance with the present invention is a method of retrieving information about one or more process variables. In accordance with the method, a magnetic implement and an analyzer for measuring the process variable are provided. The analyzer includes a housing having a display screen mounted in the housing and visible from the exterior of the housing. A plurality of magnetically-actuatable switches are mounted behind the display screen and are arranged in a pattern. A first window is displayed on the display screen. The first window includes a navigation icon associated with a second window. The navigation icon is aligned with one of the switches. The implement is placed proximate to the navigation icon so as to activate the one of the switches. In response to the activation of the one of the switches aligned with the navigation icon, the second window is displayed.

BRIEF DESCRIPTION OF THE DRAWINGS

The features, aspects, and advantages of the present invention will become better understood with regard to the following description, appended claims, and accompanying drawings where:

FIG. 30 shows a Diagnostic Summary window of the GUI;

FIG. 31 shows an Alarm Log window of the GUI;

DETAILED DESCRIPTION OF ILLUSTRATIVE EMBODIMENTS

Figure 1:
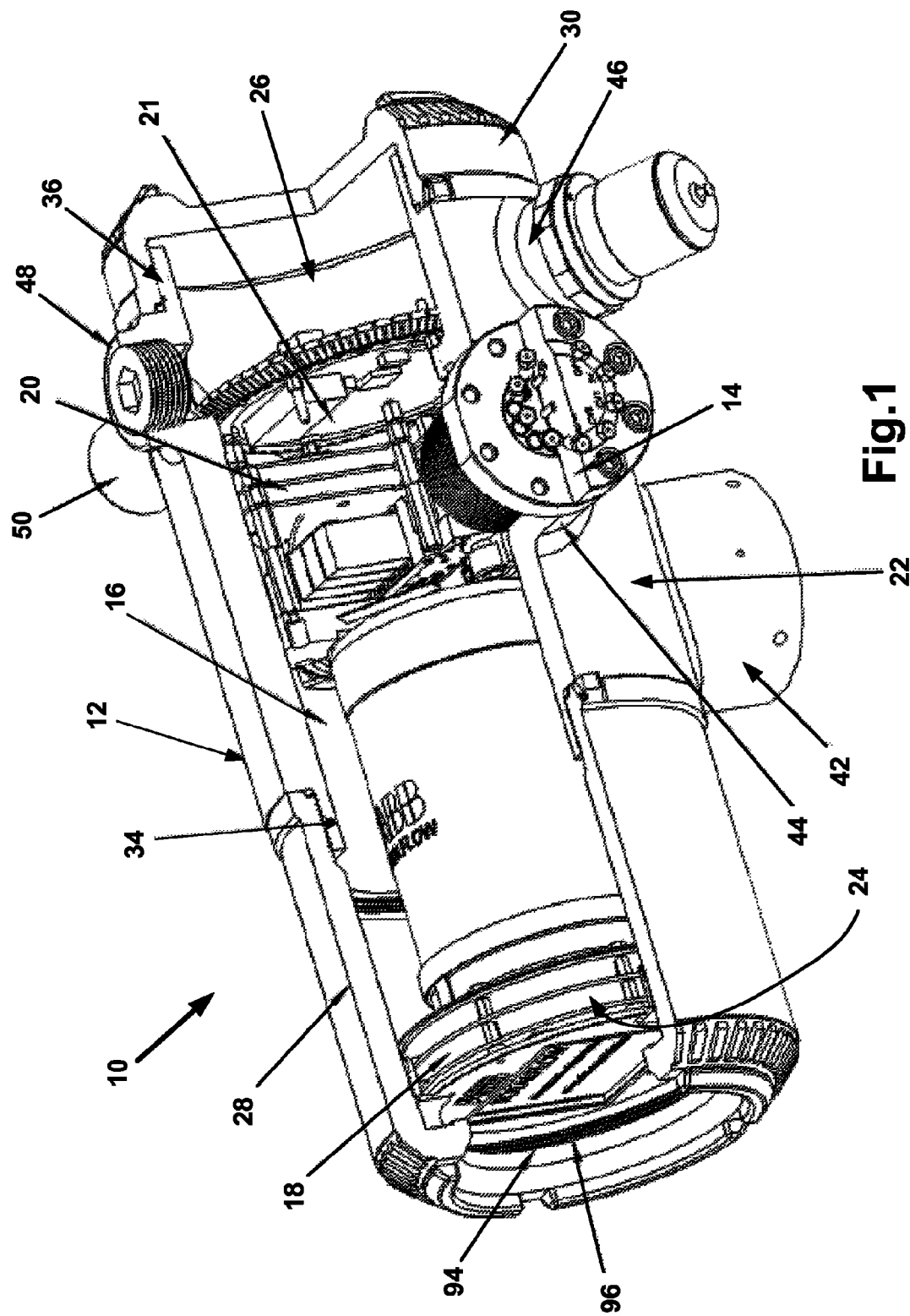
FIG. 1 shows a perspective view of a gas chromatograph with a portion cut away to better show the interior features thereof.

It should be noted that in the detailed description that follows, identical components have the same reference numerals, regardless of whether they are shown in different embodiments of the present invention. It should also be noted that in order to clearly and concisely disclose the present invention, the drawings may not necessarily be to scale and certain features of the invention may be shown in somewhat schematic form.

Below is a list of acronyms used in the specification and their respective meanings:
"CPU" shall mean "central processing unit";
"DSP" shall mean "digital signal processor";
"GC" shall mean "gas chromatograph";
"MMU" shall mean "memory management unit";
"PCA" shall mean "printed circuit assembly";
"PCB" shall mean "printed circuit board";
"RISC" shall mean "reduced instruction set computing";
"TCD" shall mean "thermal conductivity sensor"; and
"USART" shall mean a "multi-channel universal serial asynchronous receiver transmitter".

As used herein, the term "printed circuit board" (or PCB) shall mean a thin plate to which electronic components may be mounted and which has conductive pathways or traces disposed on a non-conductive substrate. The term "printed circuit board" (or PCB) shall include circuit boards that are rigid and circuit boards that are flexible or slightly flexible, i.e., flex circuits or rigid-flex circuits.

The present invention is directed to a gas chromatograph 10 having a compact and modular configuration, as well as improved operational features. The gas chromatograph 10 is adapted for mounting in the field, proximate to a source of gas that is desired to be analyzed, such as natural gas. The gas chromatograph 10 is adapted for use in harsh and explosive environments. More specifically, the gas chromatograph 10 is explosion-proof and has a NEMA 4× rating. Referring now to FIG. 1, the gas chromatograph 10 generally comprises a housing 12 enclosing a feed-through module 14, an analytical module 16, a main electronics assembly 18 having a main CPU 24, an analytical processor assembly 20 and a termination assembly 21.

I. Housing

As used herein with regard to components of the housing 12, relative positional terms such as "front", "rear", etc. refer to the position of the component in the context of the position of the gas chromatograph 10 in FIG. 1. Such relative positional terms are used only to facilitate description and are not meant to be limiting.

Figure 2:
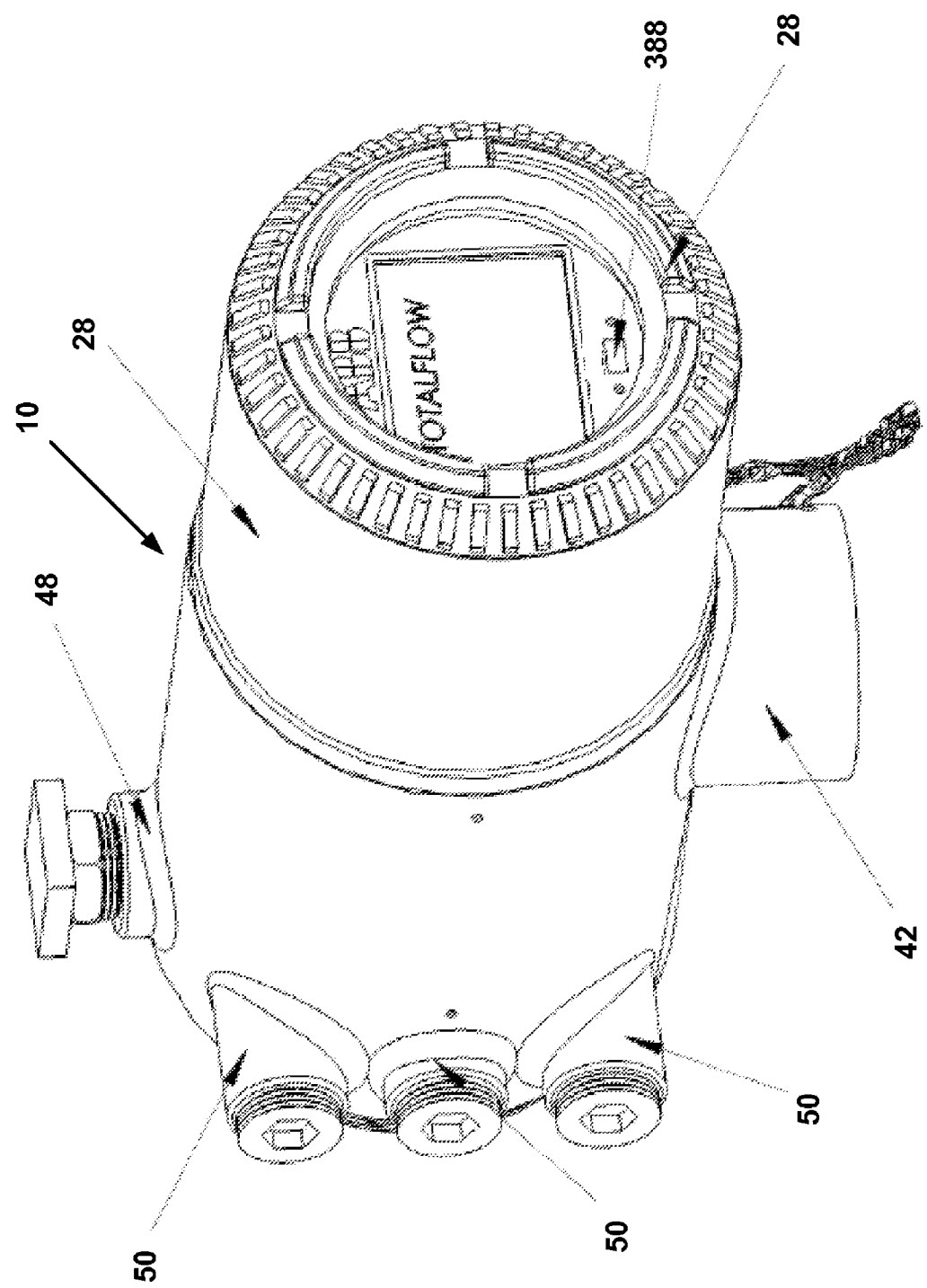
FIG. 2 shows a front perspective view of the gas chromatograph.
Figure 3:
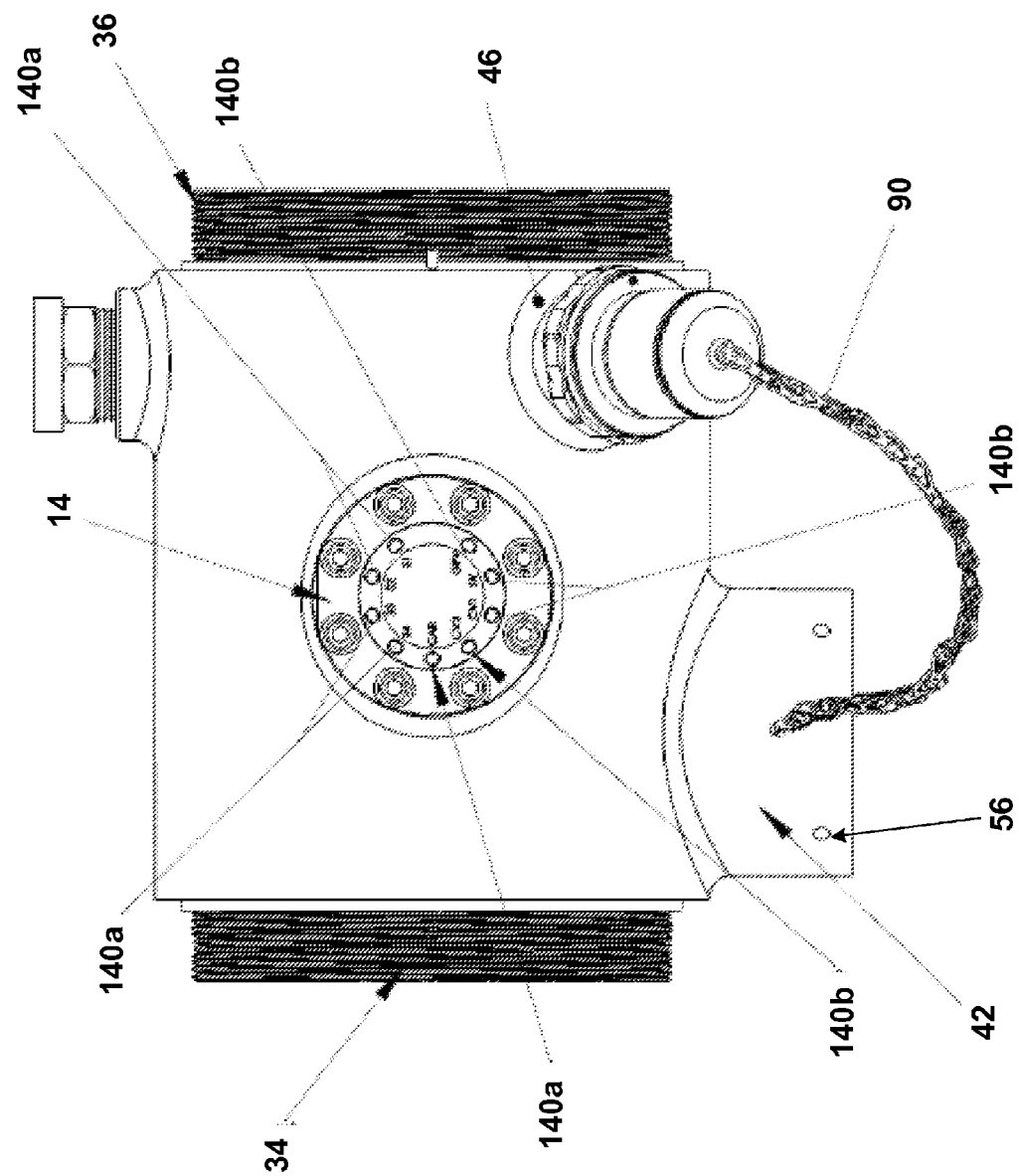
FIG. 3 shows a side view of a portion of a housing of the gas chromatograph.
Figure 4:
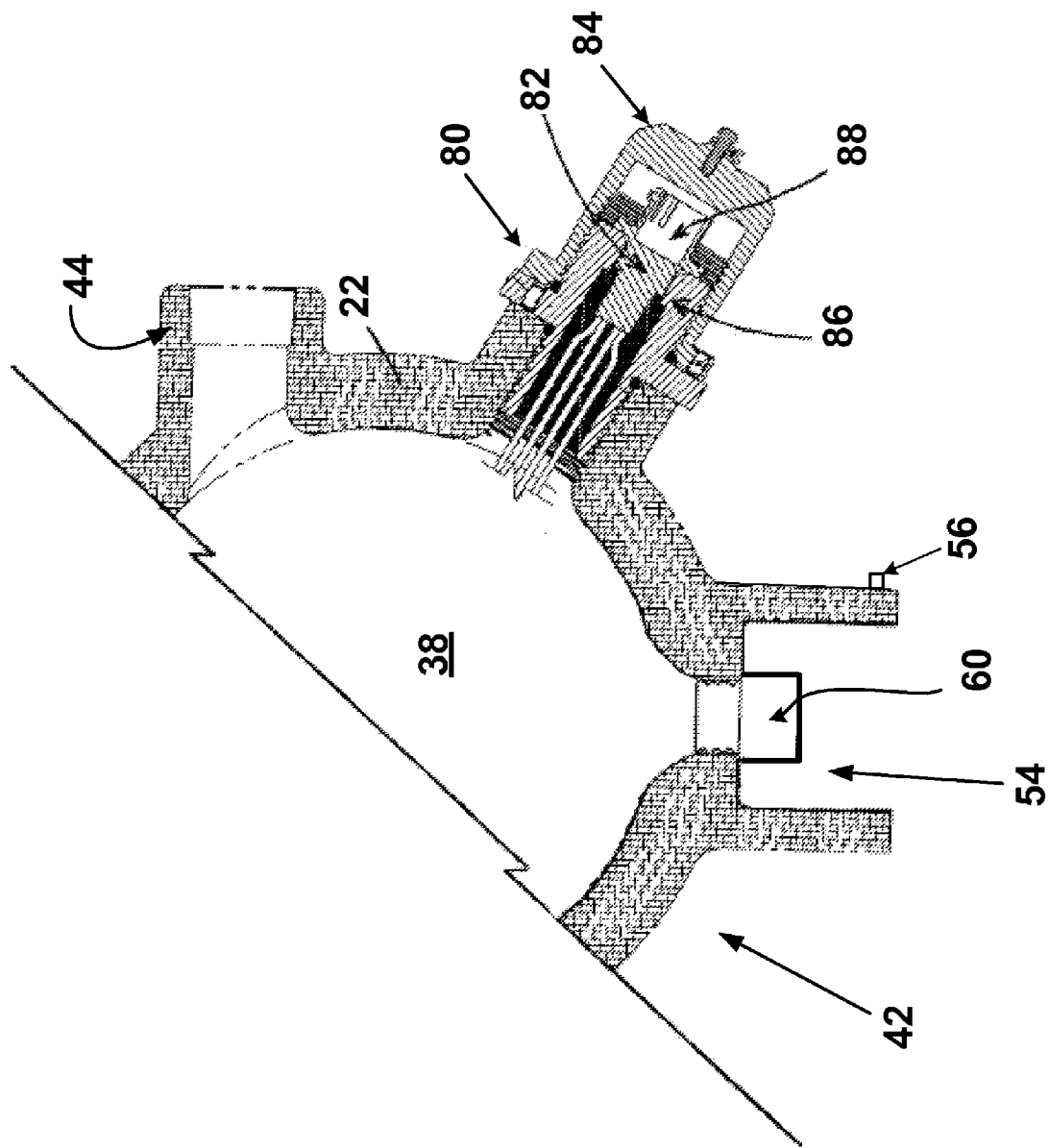
FIG. 4 shows a sectional view of a portion of the gas chromatograph showing a main mount and a first communication boss with a connector assembly mounted thereto.

Referring now also to FIGS. 2-4, the housing 12 includes a cylindrical main section 22 having front and rear access openings closed by removable front and rear access covers 28, 30, respectively. The main section 22 has a unitary construction and is comprised of a cast metal, such as aluminum or steel. The main section 22 has threaded front and rear collars 34, 36 that define the front and rear access openings, respectively. An interior surface of the main section 22 defines an interior cavity 38. A plurality of mounting ears 40 (shown in FIG. 5) are joined to the interior surface of the main section 22, around the circumference thereof and extend inwardly into the interior cavity 38. A main mount 42, a feed boss 44, first and second communication bosses 46, 48 and one or more conduit bosses 50 are joined to the main section 22 and extend outwardly therefrom.

The feed-through module 14 is removably secured to the feed boss 44 of the housing 12 by a threaded connection. When so secured, the longitudinal axis of the feed-through module 14 is disposed perpendicular to the longitudinal axes of the housing 12 and the analytical module 16.

With particular reference now to FIG. 4, the main mount 42 is cylindrical and extends vertically downward from the bottom of the central portion of the main section 22. An interior surface of the mount defines a cylindrical cavity 54 for receiving a pipe or other structure for supporting the gas chromatograph. A grounding lug 56 is attached to the exterior of the mount for electrical connection to a wire or cable electrically connected to an earth ground. A threaded breather passage extends through the main section 22 and into the interior cavity 38 of the housing 12. A breather/drain valve 60 is threaded into the breather passage. In this manner, when the gas chromatograph 10 is mounted to a pipe, the breather/drain valve 60 is disposed inside the pipe and, thus, is shielded from the outside environment.

Figure 5:
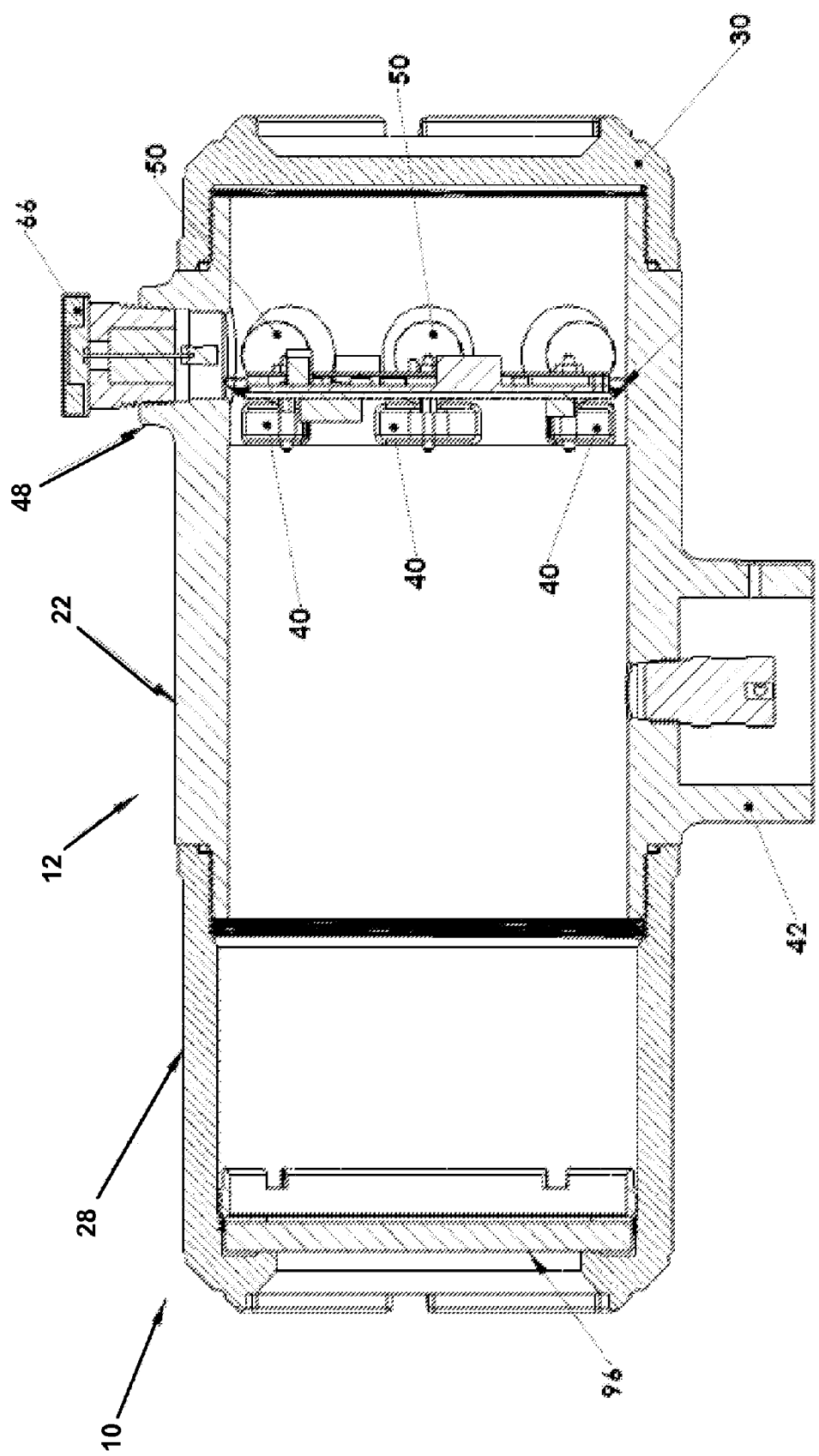
FIG. 5 shows a side sectional view of the gas chromatograph.

Referring now to FIG. 5, the second communication boss 48 is cylindrical and extends upward from a top portion of the main section 22. An interior surface of the second communication boss 48 helps defines an interior passage that extends through the main section 22 and into the interior cavity 38 of the housing 12. The interior surface has an interior thread that secures an antenna module 66 to the second communication boss 48. The antenna module 66 is capable of transmitting and receiving radio frequency (RF) energy.

Referring back to FIG. 1, the rear access cover 30 is cylindrical and has anterior and posterior ends. The anterior end has an interior thread for mating with the exterior thread of the rear collar 36 so as to removably secure the rear access cover 30 to the main section 22 and close the rear access opening 26. The posterior end has a plurality of spaced-apart and circumferentially disposed ribs. The ribs help an operator establish a grip on the rear access cover 30 when rotating the rear access cover 30 to open or close the rear access opening 26.

The front access cover 28 is cylindrical and has anterior and posterior ends. The posterior end has an interior thread for mating with the exterior thread of the front collar 34 so as to removably secure the front access cover 28 to the main section 22 and close the front access opening. The anterior end has a plurality of spaced-apart ribs circumferentially disposed around a view opening 94. The ribs help an operator establish a grip on the front access cover 28 when rotating the front access cover 28 to open or close the front access opening. The view opening 94 is closed by a transparent shield panel 96 that provides shielding against radio frequency interference (RFI).

The conduit bosses 50 have threaded openings for securing conduits to the housing 12. Interior passages extend through the conduit bosses 50 and into the interior cavity 38. When the gas chromatograph 10 is mounted in the field, first and second conduits may be secured to first and second conduit bosses 50, wherein the first conduit runs power wiring into the interior cavity 38 and the second conduit runs a communication line, such as an Ethernet cable, into the interior cavity 38. If a conduit boss 50 is not connected to a conduit, the conduit boss 50 is closed with an NPT plug.

When the gas chromatograph 10 is mounted and operating in the field unattended, the housing 12 is closed, i.e., the front and rear access covers 28, 30 are secured to the main section 22, the feed-through module 14 is secured to the feed boss 44, the conduit bosses 50 are connected to conduits or closed with NPT plugs, the second communication boss 48 is connected to the antenna module 66 or closed with an NPT plug, and the first communication boss 46 is connected to the connector assembly 80, with the cap 84 secured to the mount 86. When the housing 12 is closed as described above, the housing 12 is explosion-proof (and flame-proof) and defines a single contained volume. As used herein, the term "contained volume" shall mean that if an explosion occurs in the contained volume, the explosion will not propagate to the environment external to the contained volume. More specifically, if an explosion occurs in the contained volume, gases escaping the contained volume through any gaps or openings in the housing 12 will not be hot enough to ignite a classified hazardous location (or potentially explosive atmosphere) external to the contained volume. Specifications for certifying an enclosure as being explosion proof or flame proof are provided by certifying agencies, such as the Factory Mutual Research Corporation (FM), the Canadian Standards Association (CSA), the International Electrotechnical Commission (IEC) and the Committee for Electrotechnical Standardization (CENELEC).

Figure 6:
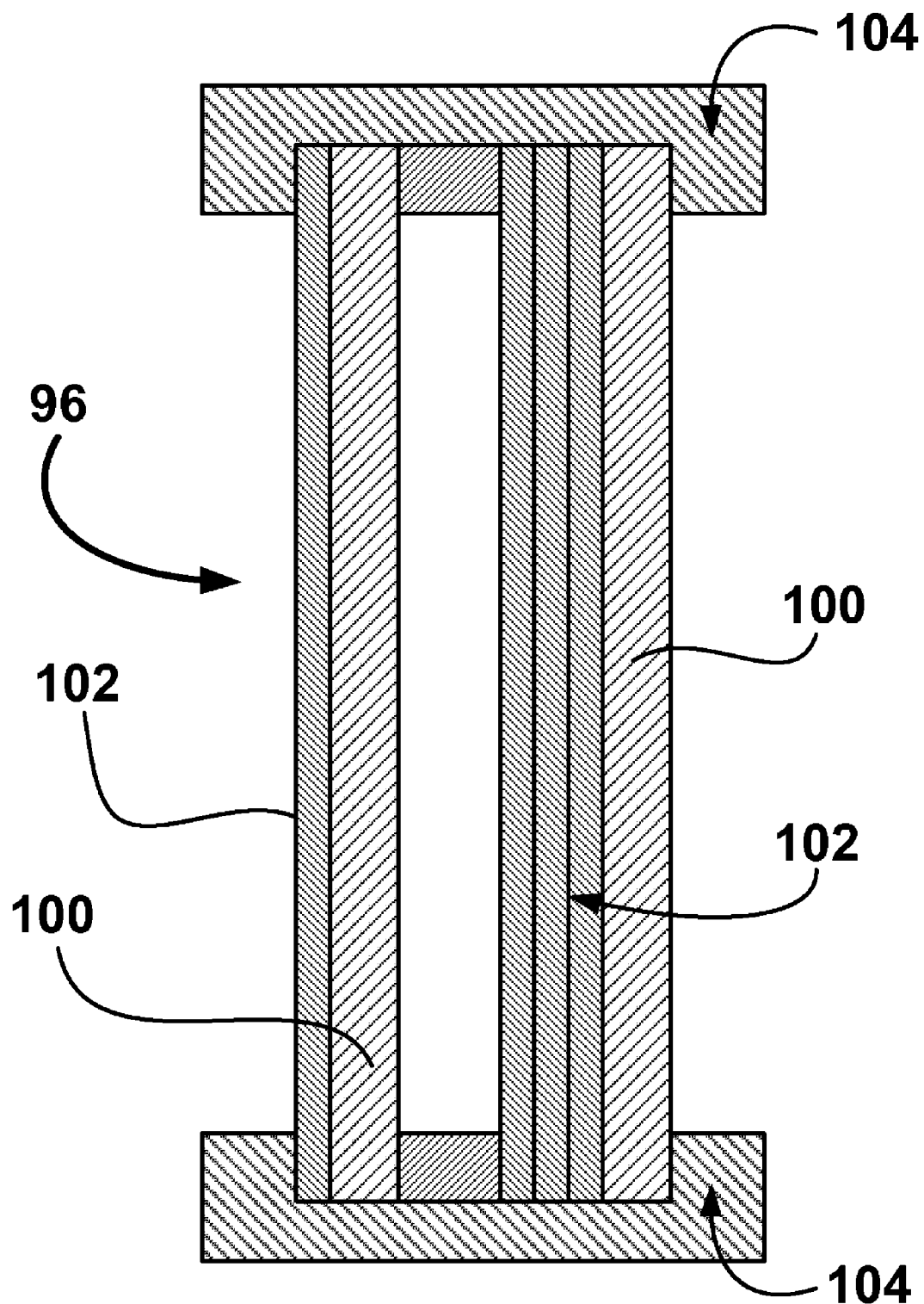
FIG. 6 shows a sectional view of a shield panel of the gas chromatograph.
Figure 7:
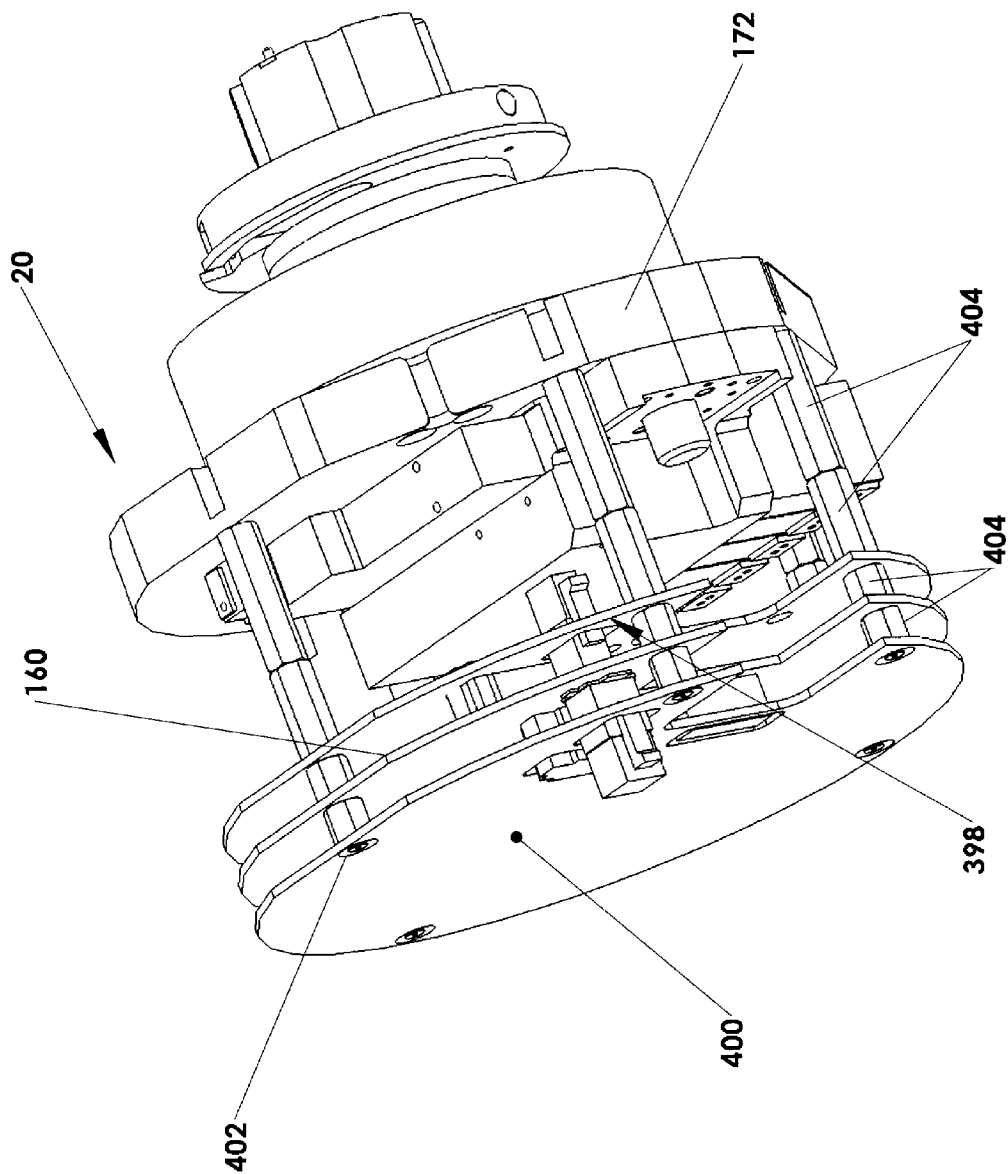
FIG. 7 shows a perspective view of an analytical processor assembly of the analytical module.

Referring now to FIG. 6, the shield panel 96 includes one or more transparent sheets 100 adjoining one or more transparent conductive layers 102. The transparent sheet 100 may be comprised of glass or plastic, and the layers 102 may be comprised of wire mesh and/or coatings. For example, in one embodiment, the shield panel 96 may comprise a wire mesh sandwiched between a pair of sheets of glass or transparent plastic. The wire mesh is comprised of a metal such as stainless steel and may be coated with one or more layers of one or more other metals, such as nickel, copper, silver, gold, aluminum, chrome, or titanium, or alloys thereof. The wire mesh may have a wire diameter between about 0.0005 to about 0.010 inch and an open area (relative to the total mesh area) between about 40% to about 75%. Examples of shield panels with wire mesh which may be used for the shield panel are disclosed in U.S. Pat. Nos. 4,247,737; 4,826,718; and 5,012,041, all of which are hereby incorporated by reference.

In other embodiments, the shield panel 96 comprises at least one sheet of glass or transparent plastic coated with at least one transparent conductive coating. Typically, each conductive coating has a thickness in a range between about 5 and about 300 nm and may be comprised of a single layer of a conductive metal, such as nickel, copper, silver, gold, aluminum, chrome, or titanium, or alloys thereof, or may be comprised of one or more layers of such a conductive metal along with one or more layers of a metal oxide, such as tin oxide, indium oxide, titanium oxide, zinc oxide, or bismuth oxide. The conductive metal layer may be directly deposited on the glass or plastic sheet and overlaid with an oxide layer, or the conductive metal layer may be sandwiched between a pair of metal oxide layers. In one embodiment, a pair of conductive metal coatings are formed on opposing major surfaces of a single sheet of glass. In another embodiment, one such conductive metal coating is deposited on a major surface of a first glass sheet and a semiconductive coating of a metal oxide, such as tin doped indium oxide (ITO) or doped tin oxide is deposited on a major surface of a second glass sheet, wherein the conductive metal coating is positioned between the two glass sheets and the semiconductive coating is positioned on the exterior of the shield panel. A conductive metal layer is typically deposited on a glass or plastic sheet by sputtering in an inert gas, such as argon, while a metal oxide layer is typically deposited on a glass or plastic sheet by reactive sputtering in an atmosphere containing an inert gas and a controlled amount of oxygen. Examples of shield panels with a conductive coating which may be used for the shield panel 96 are disclosed in U.S. Pat. Nos. 4,978,812; 5,147,694; and 5,358,787, all of which are hereby incorporated by reference.

As measured in decibels (dB) of attenuation, some embodiments of the shield panel 96 provide at least 30 dB of attenuation for frequencies in a range between 1 and 10,000 MHz. In other embodiments, the shield panel 96 provides at least 40 dB of attenuation for frequencies in a range between 1 and 10,000 MHz. In smaller frequency ranges, such as in a range between 1 and 1,000 MHz, some embodiments of the shield panel 96 provide at least 50 dB of attenuation. At a frequency of about 1,000 MHz, some embodiments of the shield panel 96 provide more than 60 dB of attenuation. It should be noted that 40 dB corresponds to an attenuation of about 99% and 60 dB corresponds to an attenuation of about 99.9%.

Although the shield panel 96 substantially blocks the transmission of electromagnetic waves having lower frequencies and longer wavelengths (such as radio, television and cell phone signals), the shield panel 96 substantially permits the transmission of electromagnetic waves having higher frequencies and shorter wavelengths (such as visible and near infrared light waves). Thus, the shield panel 96 has a visible light transmission of at least 50%. Some embodiments of the shield panel 96 have a visible light transmission of at least 60% and still other embodiments of the shield panel 96 have a visible light transmission of at least 70%.

In order to provide a direct electrical connection between the shield panel 96 and the housing 12, a conductive gasket 104 may be disposed around the view opening 94, between the shield panel 96 and the front access cover 28. The gasket 104 is compressible and may be comprised of metal-loaded rubber. The shield panel 96 may be held in place and compressed against the gasket 104 by clasps, or other types of fasteners.

II. Analytical Module

Figure 11:
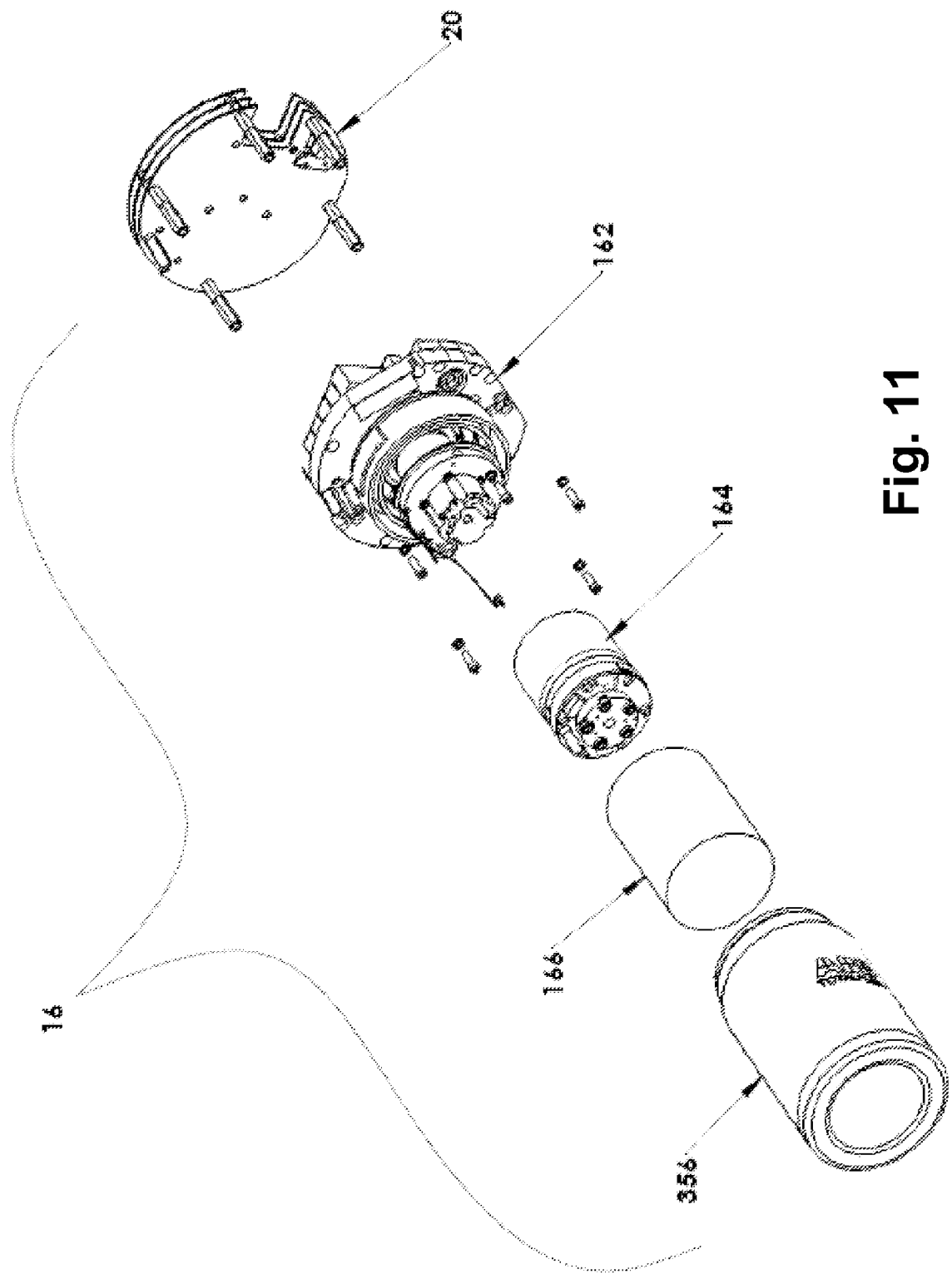
FIG. 11 shows an exploded view of the analytical module.
Figure 12:
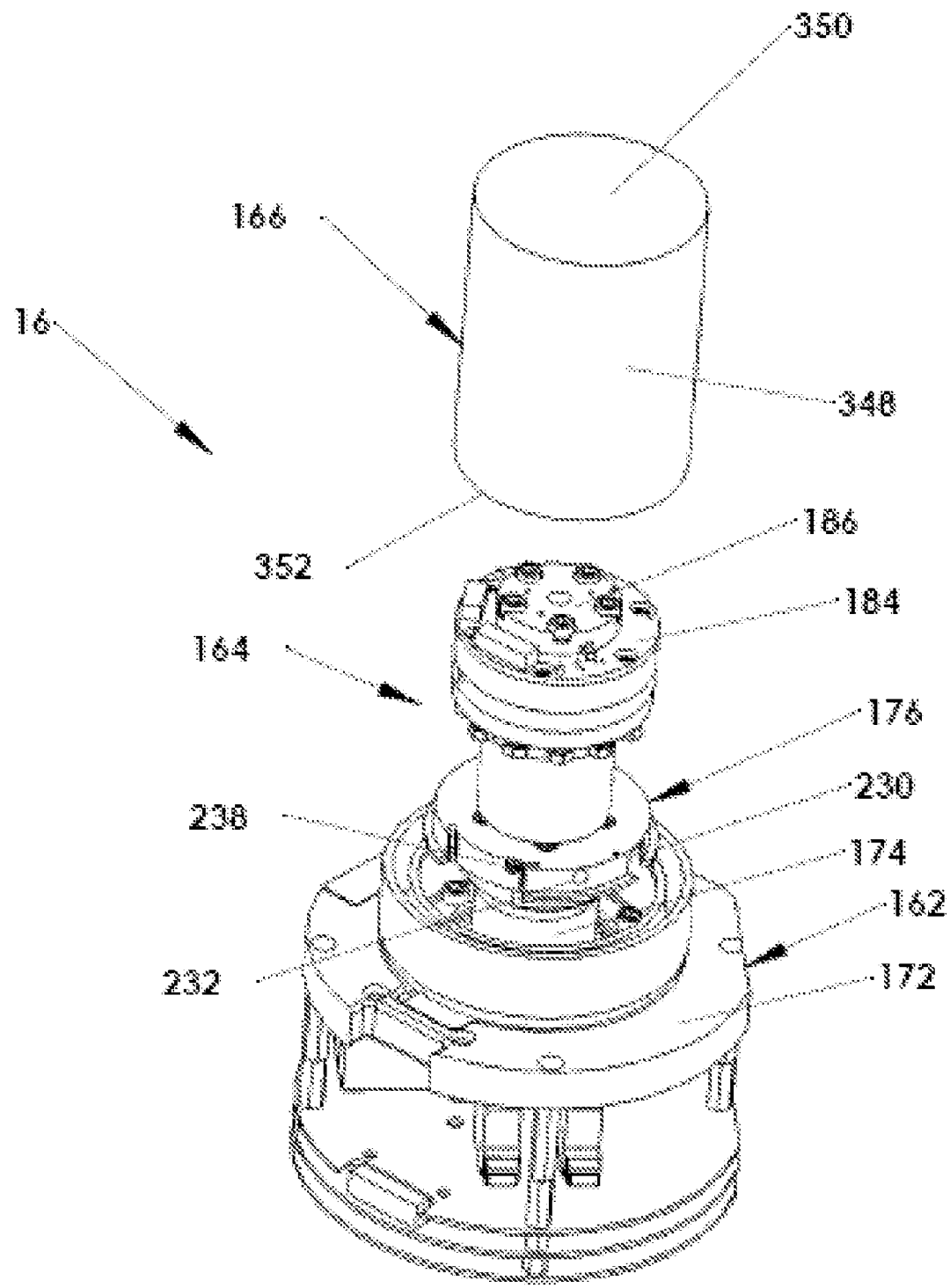
FIG. 12 shows a perspective view of the analytical module with an oven enclosure spaced above a column module.

Referring now to FIGS. 11 and 12, the analytical module 16 generally comprises a manifold module 162, a gas chromatograph (GC) module 164, an oven enclosure 166, a dewar 356 and an analytical processor assembly 20.

Manifold Module

The manifold module 162 generally includes a primary manifold plate 170 (shown in FIG. 13), a secondary manifold plate 172, a spacer 174 and a heater plate 176.

Figure 13:
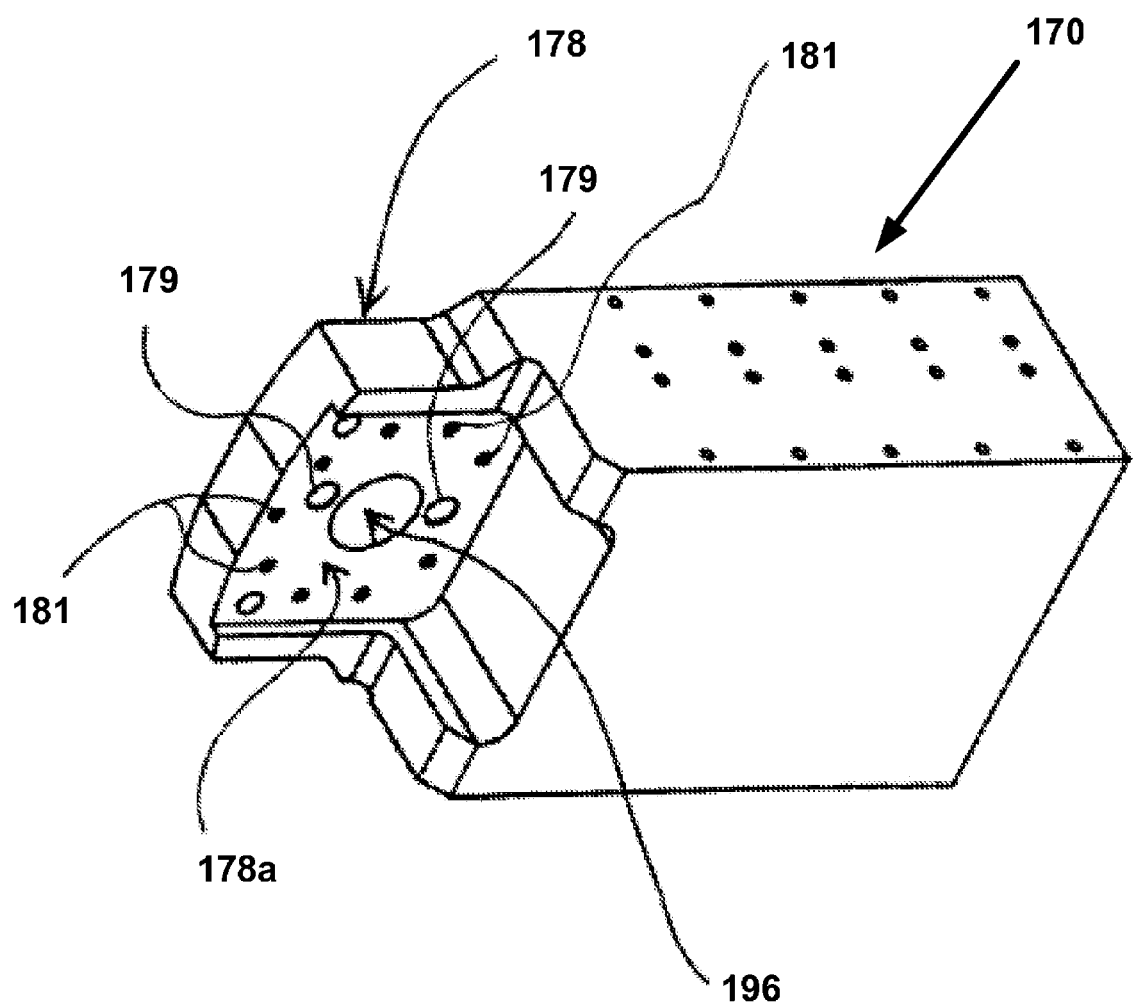
FIG. 13 shows a bottom perspective view of a primary manifold plate of the gas chromatograph without electrical flow control devices mounted thereto.
Figure 14:
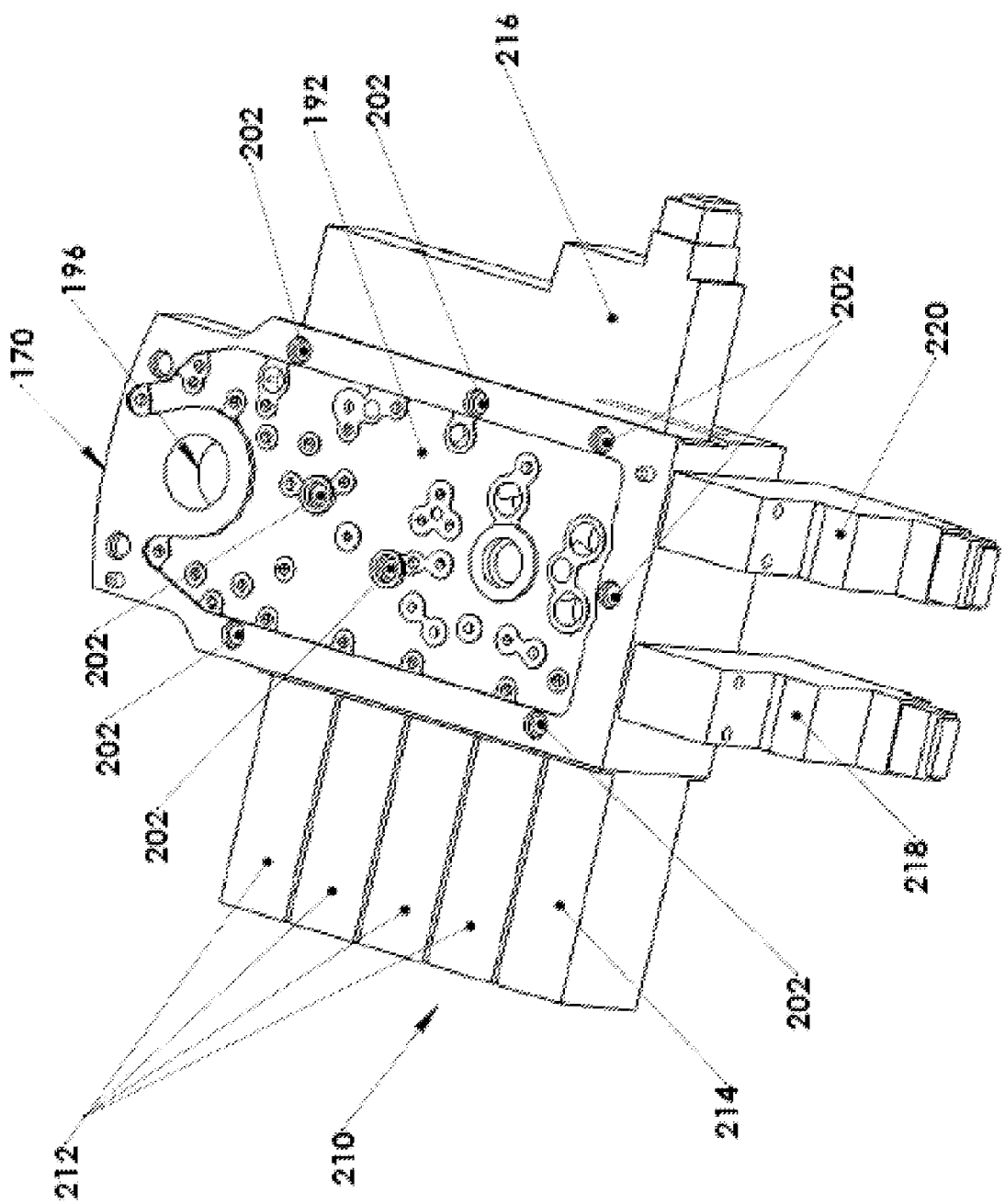
FIG. 14 shows a top perspective view of the primary manifold plate with electrical flow control devices mounted thereto.
Figure 15:
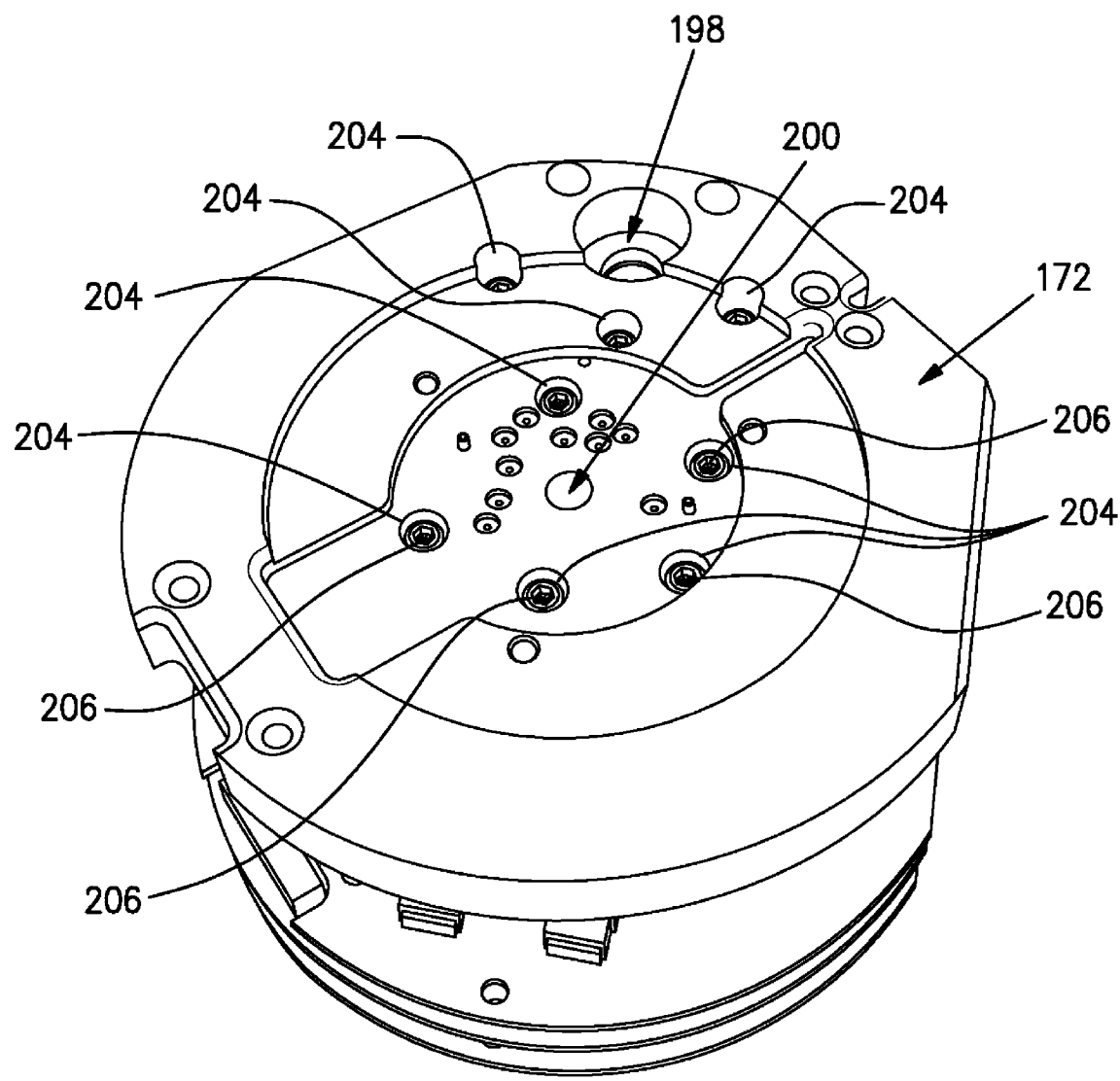
FIG. 15 shows a top perspective view of a secondary manifold plate of the gas chromatograph.

Referring now to FIGS. 13, 14 and 15, the primary and secondary manifold plates 170, 172 are each composed of a metal, such as aluminum. A gasket 192 is disposed between the primary and secondary manifold plates 170, 172. The primary manifold plate 170 includes a tongue 178 with a major face 178a that is adapted to interface with a face in the feed-through module 14. An enlarged main mounting hole 196 extends through the tongue 178. A pair of guide holes 179 and a plurality of fluid openings 181 are formed in the major face 178a and are disposed around the main mounting hole 196. When the primary manifold plate 170 is secured to the feed-through module 14, the fluid openings 181 are connected to inner passage openings in the feed-through module 14 for fluid flow therebetween. A plurality of internal fluid passages is formed in the primary manifold plate 170 so as to form a first internal passage network, which is connected to the fluid openings 181.

An enlarged, countersunk main mounting hole 198 is formed in the secondary manifold plate 172 and is aligned with the main mounting hole 196 in the primary manifold plate 170. The main mounting holes 196, 198 are used to mount the analytical module 16 to the feed-through module 14, as will be discussed further below. A central mounting hole 200 extends through the secondary manifold 172 and is disposed along the central axis thereof. A plurality of threaded mounting holes 202 are formed in the primary manifold plate 170, and a plurality of corresponding mounting holes 204 are formed in the secondary manifold plate 172. The primary manifold plate 170 is secured to the secondary manifold plate 172 by screws 206 that extend through the mounting holes 204 in the secondary manifold plate 172 and are threadably received in the holes 202 in the primary manifold plate 170. A plurality of internal fluid passages is formed in the secondary manifold plate 172 so as to form a second internal passage network. When the primary and secondary manifold plates 170, 172 are secured together, the first internal passage network of the primary manifold plate 170 is connected to the second internal passage network of the secondary manifold plate 172 for fluid flow therebetween.

Electrical flow control devices 210 are secured to the primary manifold plate 170 and are connected into the first internal passage network to control the flow of carrier gas (such as helium) and sample gas (such as natural gas) to the GC module 164 and, more particularly, to the valve assembly 180. The flow control devices 210 include sample valves 212, a shut-off valve 214, a pilot valve 216 and first and second pressure regulator valves 218, 220. The flow control devices 210 are electrically connected to and controlled by the analytical PCA 160 of the analytical processor assembly 20. The sample valves 212 are three-way, normally closed, solenoid-actuated valves that selectively control the flow of sample gas from the sample inlet paths to the first and second GC valves 188, 190. The shut-off valve 214 is a three-way, normally open, solenoid-actuated valve that controls the flow of gas from the sample valves 212 to the first and second GC valves 188, 190. The pilot valve 216 is a four way, magnetically latching solenoid actuated valve that pneumatically controls the actuation of the first and second GC valves 188, 190. The first and second pressure regulators 218, 220 are proportional solenoid valves for controlling the pressure of the carrier gas supplied to the first and second GC valves 188, 190. Actuation of one of the sample valves 212 will cause gas from the sample line associated with the actuated sample valve 212 to be supplied to the first and second GC valves 188, 190, assuming the shut-off valve 214 is open.

Figure 16:
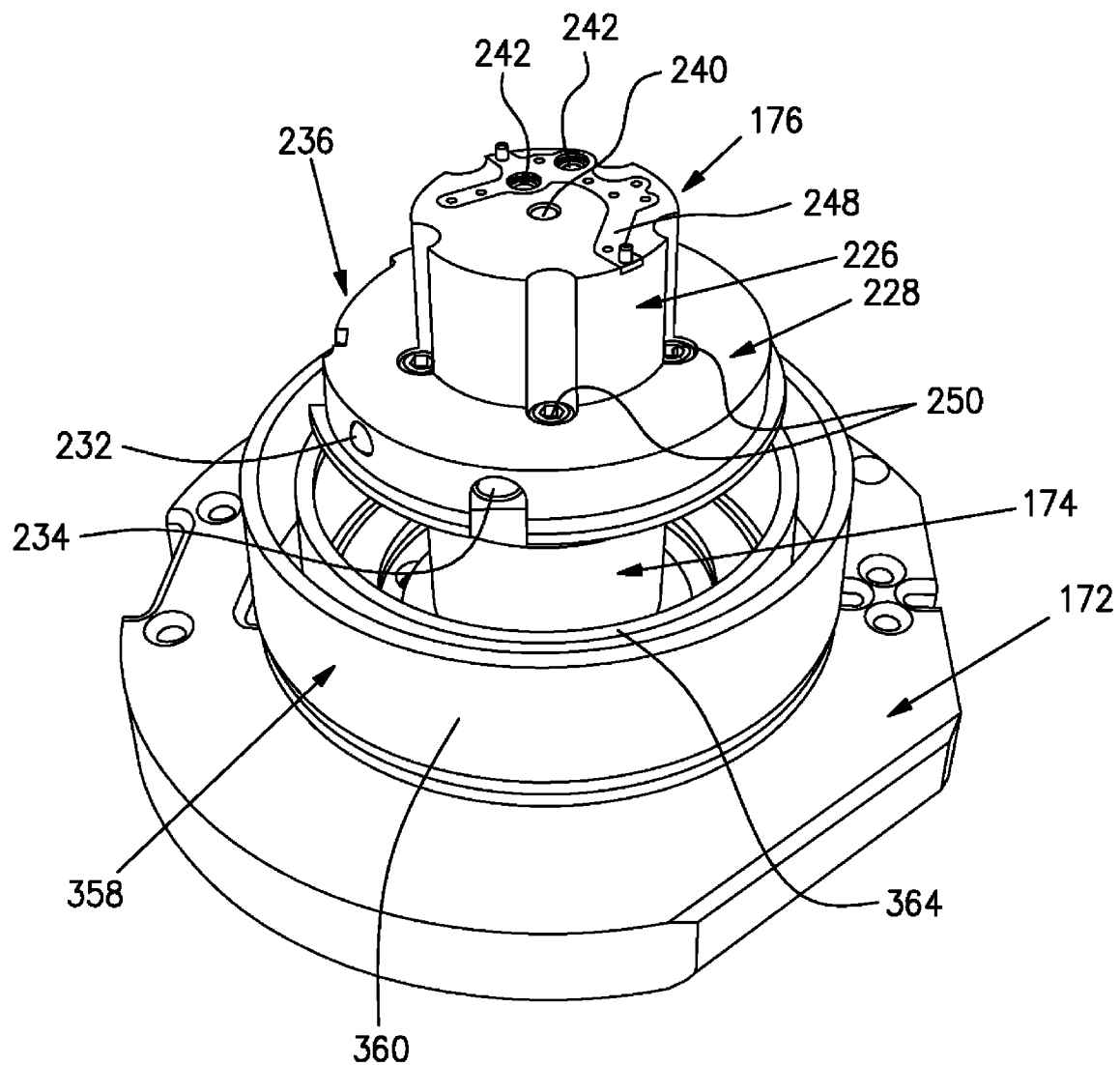
FIG. 16 shows a top perspective view of a spacer and a heater plate mounted to the secondary manifold plate.

Referring now to FIG. 16, the spacer 174 is composed of an insulating material, such as an insulating plastic or ceramic. In one embodiment, the spacer 174 is composed of chlorinated polyvinyl chloride (CPVC), which has good insulating properties and is heat and chemical resistant. The spacer 174 includes a cylindrical body with an annular flange disposed at an upper end thereof. A countersunk bore extends through the spacer 174 along the center axis thereof. A plurality of mounting holes with threaded inserts (or threaded holes) extend through the spacer 174 and are disposed around the countersunk bore. The spacer 174 is secured to the secondary manifold plate 172 by a single threaded bolt with a socket head, which extends through the countersunk bore, the central mounting hole 200 in the secondary manifold 172 and into a threaded bore in the primary manifold plate 170. The spacer 174 spaces the heater plate 176 above the secondary manifold plate 172 and limits thermal communication between the heater plate 176 and the secondary manifold plate 172. Internal flow passages for sample gas, carrier gas, vent gas, etc. extend through the spacer 174 and form a third internal passage network, which is connected to the second internal passage network of the secondary manifold plate 172.

The heater plate 176 is composed of aluminum or other conductive metal and comprises a generally cylindrical pillar 226 joined to a generally cylindrical pedestal 228 with an annular flange 230. A plurality of mounting holes are disposed around the pedestal 228 and extend longitudinally therethrough. A pair of bearings 232 are mounted in sockets formed in diametrically opposite portions of a side surface of the pedestal 228. A cartridge heater 234 is mounted in a tunnel that extends through the side surface of the pedestal 228. The cartridge heater 234 is electrically connected to and controlled by the analytical PCA 160 in the analytical processor assembly 20. An enlarged longitudinally-extending channel 236 is formed in the pedestal 228 and extends through the flange 230. The channel 236 accommodates a ribbon cable 237 (shown schematically in FIG. 8) that connects the GC PCBA 184 to the analytical processor assembly 20. An oven temperature sensor 238 (shown in FIG. 12 and schematically in FIG. 9) is mounted in a well that is formed in the pedestal 228 and is located in the channel 236. A threaded central bore 240 is formed in the pillar 226 of the heater plate 176 and extends along the center axis thereof. Outward from the central bore 240, a pair of sample conduits are formed in the pillar 226 and extend longitudinally therein. Each of the sample conduits includes a narrow inlet portion and an enlarged main portion, which is defined by a helically threaded interior wall. Cylindrical inserts 242 (shown in FIG. 16) composed of metal are disposed in the main portions of the sample conduits. In each sample conduit, the threaded interior wall cooperates with the insert to define a helical sample passage 244 that extends through the heater plate 176. The helical sample passages 244 are connected in series by a sample pressure sensor 246 in the valve assembly 180, as is schematically shown in FIGS. 41 and 42. The interconnected helical sample passages 244 increase the residence time of the sample gas in the heater plate 176, thereby improving the heating of the sample gas. An irregular gasket 248 is secured by pins to an upper end surface of the pillar 226. The heater plate 176 is secured to the spacer 174 by screws 250 that extend through the mounting holes in the heater plate 176 and are threadably received in the inserts in the mounting holes in the spacer 174. The helical sample passages 244 along with other internal flow passages for carrier gas, vent gas, etc. extend through the heater plate 176 and form a fourth internal passage network, which is connected to the third internal passage network of the spacer 174.

A cap 358 for engagement with the dewar 356 is secured to the secondary manifold plate 172. The cap 358 is composed of plastic and includes a cylindrical outer side wall 360 joined at a rounded edge to an annular end wall 362. An interior surface of the outer side wall 360 is threaded. A central portion of the end wall 362 has a recessed exterior surface and a plurality of holes extending therethrough. A cylindrical interior wall 364 is joined to an interior surface of the end wall 362 and extends upwardly therefrom. A metal clamp ring 366 with a plurality of holes formed therein is disposed radially inward from the interior wall 364 and adjoins an interior surface of the central portion of the end wall 362. Screws 368 extend through the holes in the clamp ring 366 and the cap 358 and are received in threaded openings in the secondary manifold plate 172, thereby securing the clamp ring 366 and, thus, the cap 358 to the secondary manifold plate 172.

GC Module

Figure 27:
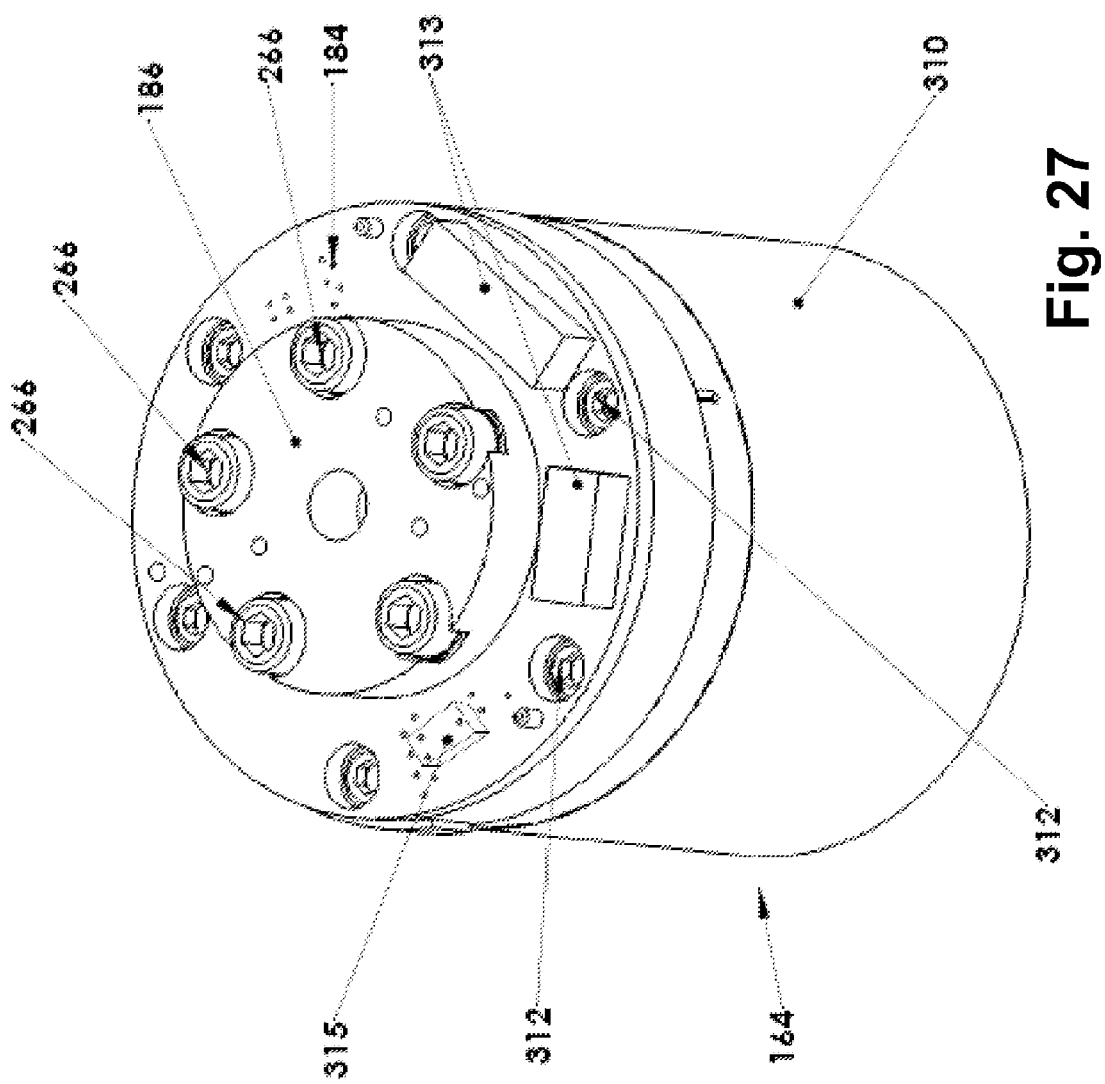
FIG. 27 shows a perspective view of the GC module.

The GC module 164 generally comprises a valve assembly 180, a column assembly 182, a GC PCBA 184 and a cover plate 186. FIG. 27 shows the GC module 164 fully assembled.

A plurality of internal flow passages for sample gas, carrier gas, vent gas, etc. extend through the valve assembly 180 and form a fifth internal passage network, which is connected to the fourth internal passage network of the heater plate 176. The fifth internal passage network comprises first and second GC valves 188, 190.

Figure 17:
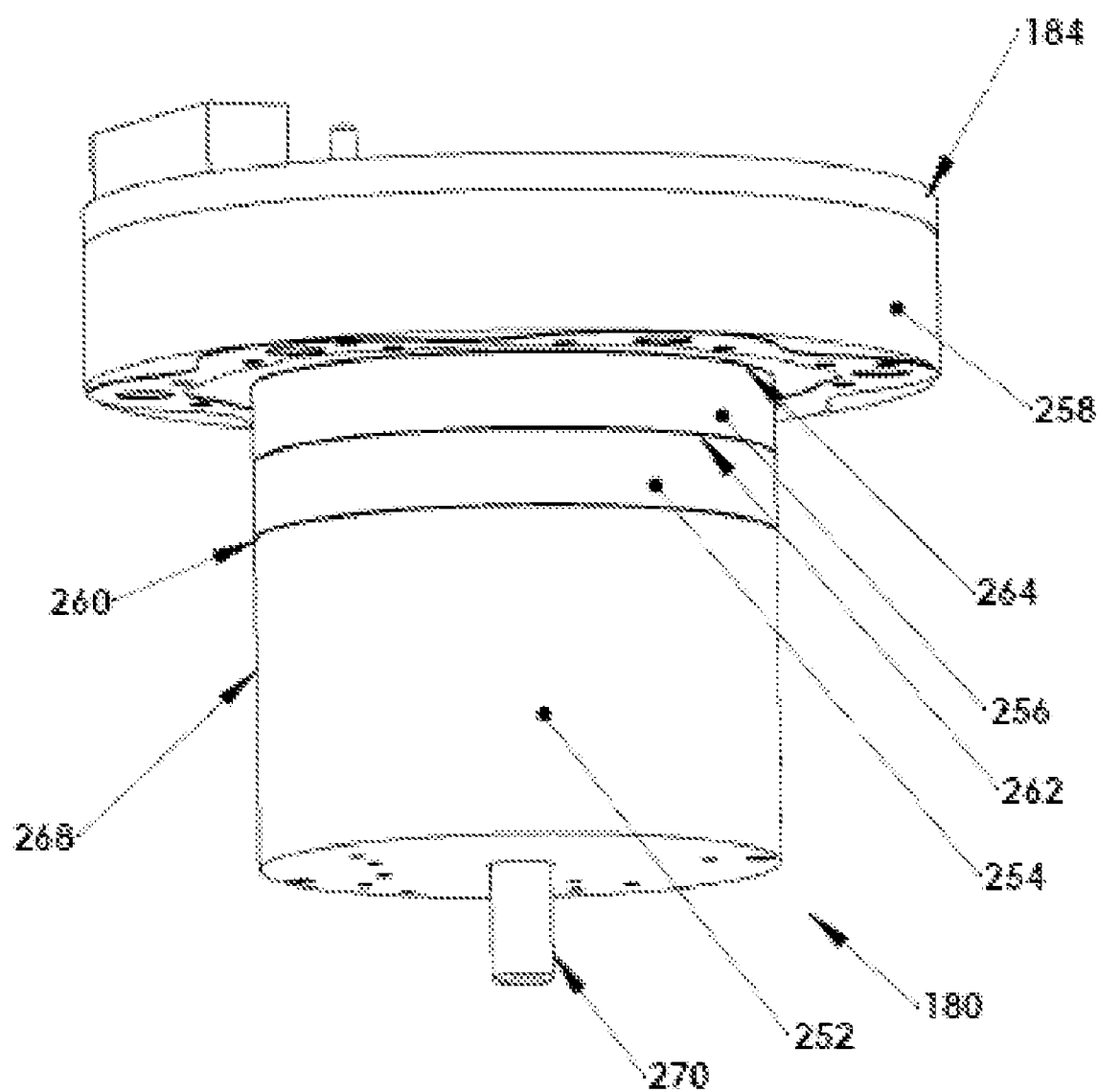
FIG. 17 shows a perspective view of a valve assembly of a GC module of the gas chromatograph.
Figure 18:
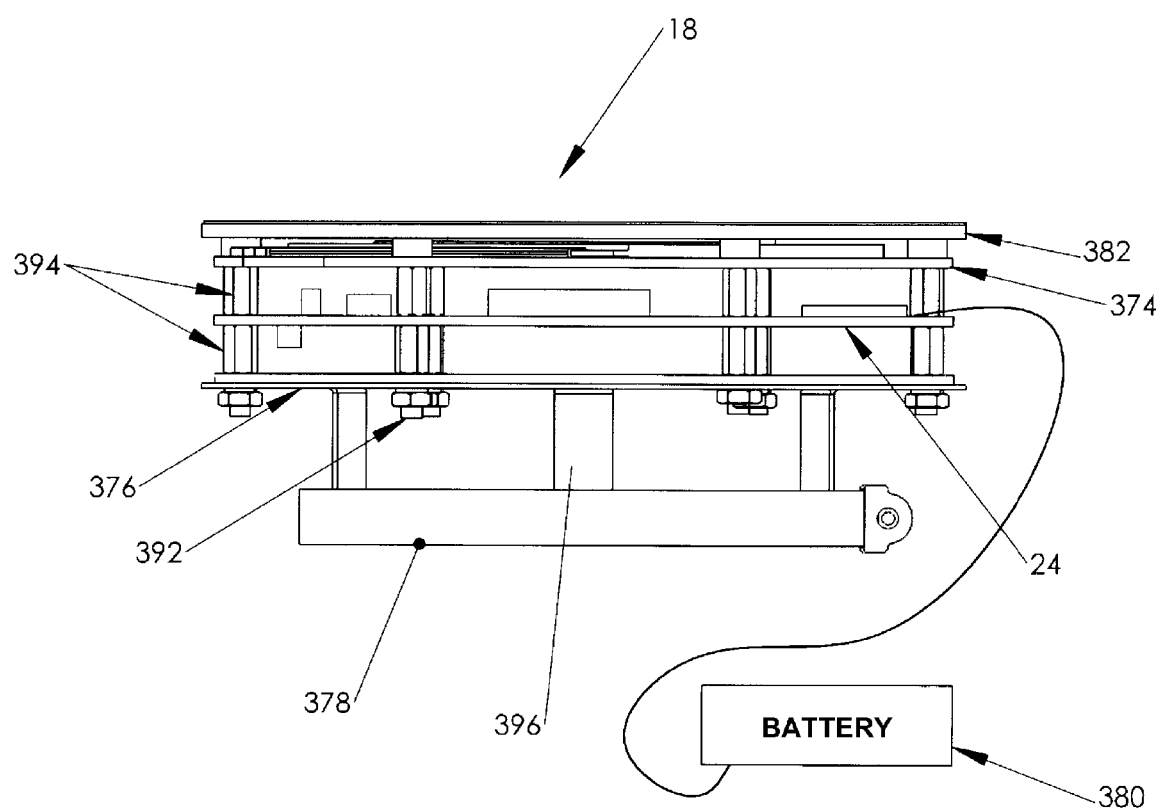
FIG. 18 shows a side elevational view of a main electronics assembly of the gas chromatograph.

Referring now to FIG. 17, the valve assembly 180 includes a first valve plate 252, a second valve plate 254, a third valve plate 256 and a detector plate 258. The first valve plate 252 has a cylindrical side surface and upper and lower end surfaces. A first diaphragm 260 is disposed between the upper end surface of the first valve plate 252 and a lower end surface of the second valve plate 254, while a second diaphragm 262 is disposed between an upper end surface of the second valve plate 254 and a lower end surface of the third valve plate 256. A gasket 264 is disposed between an upper end surface of the third valve plate 256 and a lower end surface of the detector plate 258. The first valve plate 252, the second and third valve plates 254, 256 and the detector plate 258 are coaxially disposed and are secured together by a plurality of screws 266 that extend through the cover plate 186, the GC PCBA 184, the detector plate 258 and the second and third valve plates 254, 256 and are threadably received in openings in the first valve plate 252. The first valve plate 252 and the second and third valve plates 254, 256 have substantially the same diameters so as to form a mandrel 268 for the column assembly 182. The mandrel 268 has a substantially smaller diameter than the detector plate 258. In this manner, when the column assembly 182 is mounted to the mandrel 268, the column assembly 182 abuts against an annular portion of the lower end surface of the detector plate 258, which is disposed radially outward from the mandrel 268. The valve assembly 180 is secured to the heater plate 176 by an elongated bolt 270 that extends through the center of the cover plate 186, the GC PCBA 184 and the valve assembly 180 and is threadably received in the central bore 240 of the heater plate 176.

An upper end surface of the first valve plate 252, the first diaphragm 260 and a lower end surface of the second valve plate 254 cooperate to define the first GC valve 188 (shown schematically in FIGS. 41 and 42), while an upper end surface of the second valve plate 254, the second diaphragm 262 and a lower end surface of the third valve plate 256 cooperate to define the second GC valve 190 (shown schematically in FIGS. 41 and 42). Each of the GC valves 188, 190 have ports 1-10 (see FIGS. 41 and 42). The ports 1-10 of the first GC valve 188 are formed in the first valve plate 252, while the ports 1-10 of the second GC valve 190 are formed in the third valve plate 256. The first and second GC valves 188, 190 each have two modes, namely an "inject" mode and a "backflush" mode.

Referring now to FIGS. 18-22, the second valve plate 254 is cylindrical and includes the upper and lower end surfaces, respectively. A central bore 271 extends through the valve plate 254, along the central axis thereof. Radially outward from the central bore 271, an annular upper manifold groove 272 is formed in the upper end surface 254$a$ and an annular lower manifold groove 273 is formed in the lower end surface 254$b$. The upper manifold groove 272 is connected to an internal first carrier gas passage 267, while the lower manifold groove 273 is connected to an internal second carrier gas passage 269. The first and second carrier gas passages are connected to the pilot valve 216 for receiving carrier gas therefrom. The pilot valve 216 only provides carrier gas to one of the first and second carrier gas passage and, thus, one of the upper and lower manifold grooves 272, 273, at a time. When the upper manifold groove 272, but not the lower manifold groove 273, is provided with carrier gas, the first and second GC valves 188, 190 are in the "backflush" mode. Conversely, when the lower manifold groove 273, but not the upper manifold groove 272, is provided with carrier gas, the first and second GC valves 188, 190 are in the "inject" mode.

Figure 25:
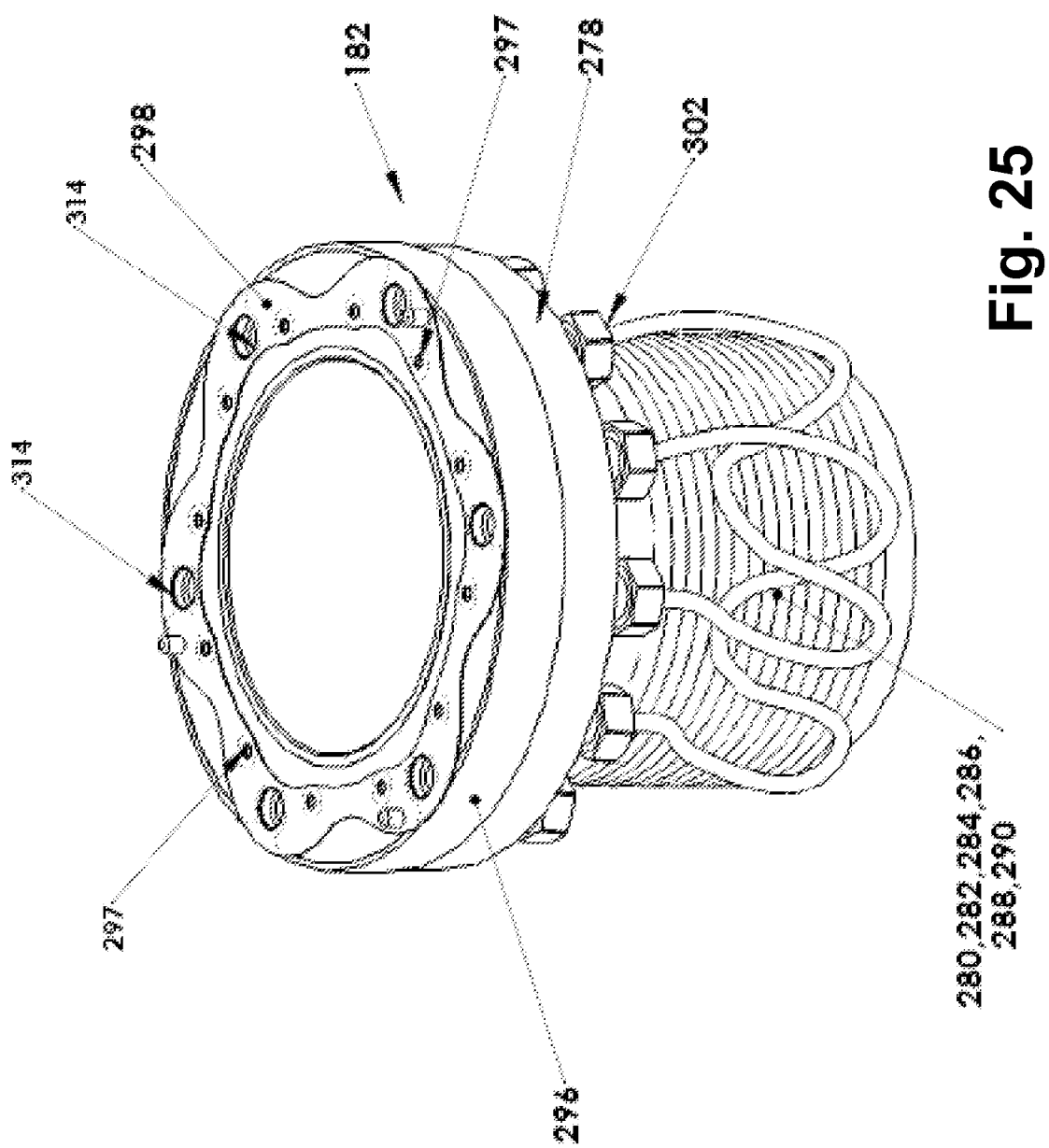
FIG. 25 shows a perspective view of a column assembly of the GC module.

As shown in FIG. 25, the column assembly 182 generally includes a spool 278, first preliminary column 280, first column 282, a second preliminary column 284, a second column 286 and first and second sample loops 288, 290.

Figure 26:
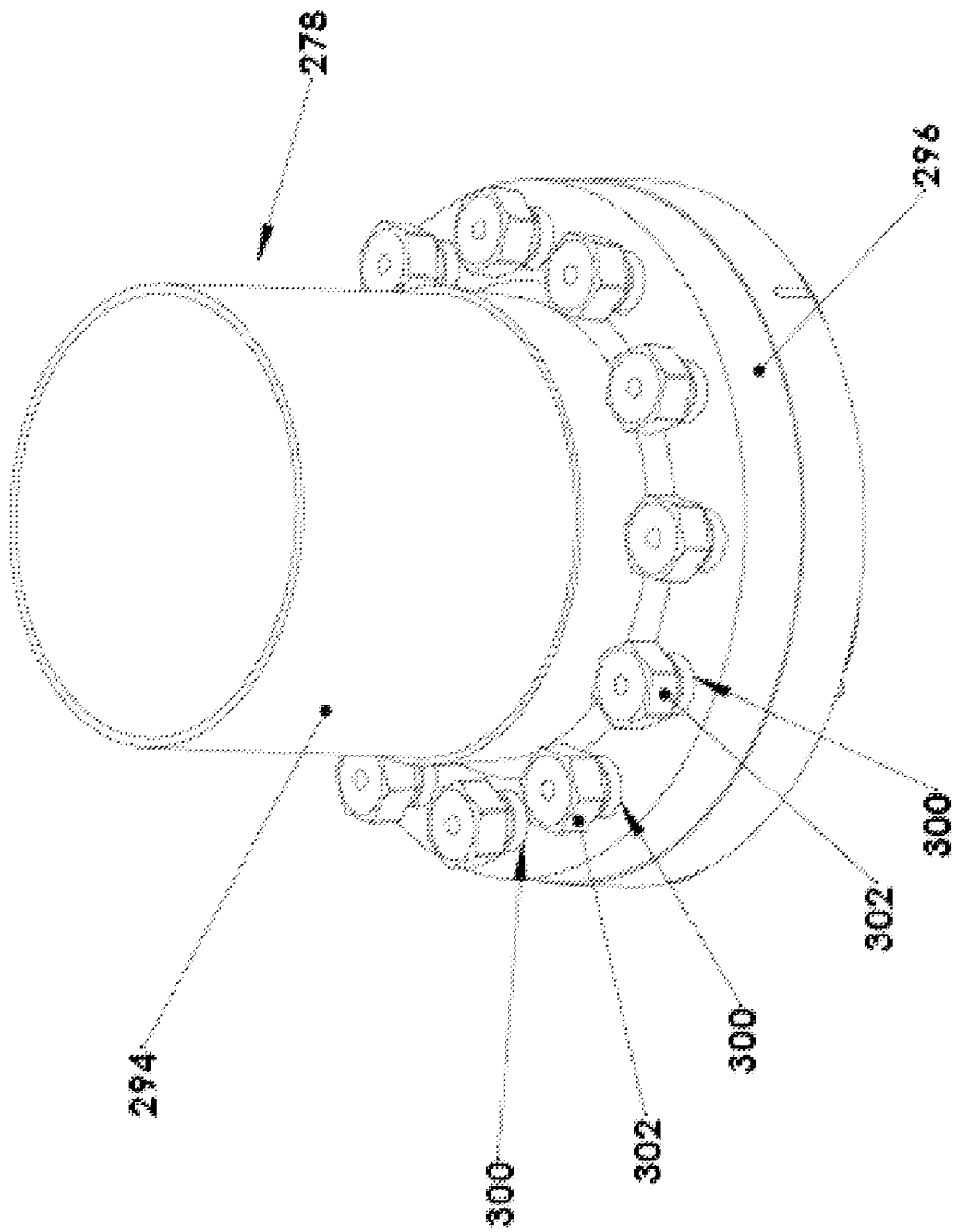
FIG. 26 shows a perspective view of a spool of the column assembly.

Referring now to FIG. 26, the spool 278 includes a hollow cylindrical body 294 with open upper and lower ends and an annular flange 296 disposed around the upper end. A plurality of flow openings 297 are formed on a top side of the flange 296. A gasket 298 is secured by pins to the top side of the annular flange 296. The gasket 298 has openings aligned with the flow openings 297 in the flange 296. On a bottom side of the flange 296, a plurality of threaded openings 300 are disposed around the flange 296. The flange 296 has a plurality of internal passages that connect the flow openings 297 to the openings 300. These internal passages form a sixth internal passage network. Ends of the columns and sample loops 280-290 are connected to fitting assemblies 302 threadably secured in the openings 300, respectively. Each fitting assembly 302 may be a compression fitting comprising a male nut 304 and a ferrule 306. The male nuts 304 are threadably secured in the openings 300 and extend outwardly therefrom, while the ferrules 306 are disposed in the openings 300 and are compressed by the male nuts 304. The ends of the columns and sample loops 280-290 extend through the male nuts 304 and the ferrules 306 and are held in place in the openings 300 by the compression of the ferrules 306. Disc-shaped filters 308 are secured over the ends of the columns and sample loops 280-290 inside the openings 300. The filters 308 are comprised of sintered stainless steel with 0.5 micron openings.

The columns 280-286 are packed columns, each of which may be comprised of a stainless steel tube having an inner diameter of 2 to 4 mm and a length of 1 to 4 meters. Each tube is packed with a suitable adsorbent, which may be organic and/or inorganic, and which is ground and screened to provide a range of particle sizes that extend from about 30 mesh to about 120 mesh. Ends of each tube contain stainless steel braided cable terminations to retain the adsorbent. In addition, the filters 308 in the openings 300 of the spool 278 help prevent migration of the adsorbent. It should be appreciated that in lieu of being packed columns, the columns 280-286 may instead be open tubular columns, such as fused silica open tubular (FSOT) columns. A FSOT column comprises a fused silica tube having an exterior polyimide coating and an interior stationary phase coating comprising a support and an adsorbent. It should also be appreciated that the gas chromatograph of the present invention is not limited to four columns and two sample loops. The gas chromatograph of the present invention may have any number of columns and sample loops, provided there is at least one column and at least one sample loop.

The columns and the sample loops 280-290 are wound around the body 294 of the spool 278 and have their ends secured to the fitting assemblies 302 as described above. The columns and the sample loops 280-290 may be wound by hand or by machine. In addition, the columns and the sample loops 280-290 may be wound directly on the spool 278, or on a separate device and then transferred as a coil to the spool 278. After the columns and sample loops 280-290 are wound around the spool 278 and connected to the fitting assemblies 302, the wound columns and the wound sample loops 280-290 are fully encapsulated in a thermal resin 310, i.e., a resin that is electrically insulating and thermally conductive. An example of a thermal resin is an epoxy resin filled with a conductive metal or metal compound, such as silver, alumina or aluminum nitride. The thermal resin 310 secures the columns and the sample loops 280-290 in position and provides greater isothermal heating and thermal stability of the columns and the sample loops 280-290.

The column assembly 182 is secured to the valve assembly 180 by a plurality of radially-outward screws 312 that extend through the GC PCBA 184 and the detector plate 258 and are threadably received in openings 314 in the flange 296 of the spool 278. When the column assembly 182 is secured to the valve assembly 180, the mandrel 268 extends through the upper end of the spool body 294 and the pillar 226 of the heater plate 176 extends through the lower end of the spool body 294, with both the mandrel 268 and the pillar 226 being disposed inside the spool body 294 and abutting against each other. In addition, the top side of the flange 296 of the spool 278 abuts the annular portion of the lower end surface of the detector plate 258. With the flange 296 and the detector plate 258 so positioned, the flow openings 297 in the flange 296 are connected to flow opening in the detector plate 258, thereby connecting the fifth internal passage network in the valve assembly 180 to the sixth internal passage network in the spool 278. The gasket 298 of the spool 278 abuts against the annular portion of the lower end surface of the detector plate 258.

The GC PCBA 184 is secured to the detector plate 258 by the radially-outward screws 312, the screws 266 and by the bolt 270. The GC PCBA 184 includes electrical connectors 313 and memory 315 mounted to a top side of a disc-shaped circuit board 316. The memory 315 may be electrically erasable programmable read-only memory (EEPROM). The memory 315 stores factory calibration information, chromatographic calibration constants, peak times, settings for the first and second pressure regulator valves 218, 220 and electronic identification of the gas chromatograph 10 and/or the GC module 164, including serial number, revision level and build date. The GC PCBA 184 also includes a first reference TCD 318, a first sensor TCD 320, a second reference TCD 322, a second sensor TCD 324, first and second carrier pressure sensors 326, 328 and the sample pressure sensor 246, all of which are secured to a bottom side of the circuit board 316 and extend downwardly therefrom. When the GC PCBA 184 is secured to the valve assembly 180, the TCDs 318-324 and the pressure sensors 246, 326, 328 extend into openings 332-344 in an upper side of the detector plate 258, respectively, and become connected into the fifth internal passage network of the valve assembly 180. The GC PCBA 184 is connected to the analytical PCA 160 by the ribbon cable 237 (shown schematically in FIG. 8).

The TCDs 318-324 can be any of a number of types of temperature sensing elements, including but not limited to negative temperature coefficient thermistors ("NTC thermistors"), or platinum RTD's, etc. These temperature sensing elements have a resistance value that varies as a function of temperature. NTC thermistors are the most common due to their high thermal sensitivity, or resistance versus temperature relationship. The term "thermistor bead" or just "bead" is sometimes used interchangeably since the sensing device is often a sensing element coated in glass and suspended on wires between two mounting posts or other support structure.

A thermistor (such as the second TCD 320) is heated by passing a current through it in such a way that it elevates its own temperature and correspondingly changes its own resistance, until its reaches a point of equilibrium such that the energy used to heat the thermistor is balanced by the energy that is dissipated or lost. The rate of energy lost by the thermistor is due to the combination of its own temperature, the thermal conductivity of its own support structure, the thermal conductivity, temperature, heat capacity and flow rate of the surrounding gas, and the temperature of the wall of the cavity or chamber that houses it. This mode of operation for the thermistor is referred to as the self-heated mode. Since the temperature of the chamber wall that the thermistor is placed in is held fairly constant at one temperature in most chromatographic applications, the variables that modulate the thermistor's heat loss the most are related to the physical properties of the gas flowing by it. Therefore, the gas chromatograph 10 minimizes the changes in the pressure of the gas as well as its flow rate in the vicinity of the thermistor. This is done in an effort to minimize the amount that these variables modulate the energy loss of the thermistor leaving the thermal conductivity of the gas as the prime variable of measurement. The heat capacity of the gas also contributes to the detector response, but is less significant.

Although the gas chromatograph 10 is described as using TCDs, it should be appreciated that other detectors are available and may be used in the gas chromatograph.

Oven Enclosure

Referring back to FIG. 12, the oven enclosure 166 is composed of a conductive metal, such as stainless steel or aluminum, and has a cylindrical side wall 348, a top end wall 350, and a circular bottom edge 352 defining a bottom opening. An annular groove is formed in an inside surface of the side wall 348. The oven enclosure 166 is disposed over the GC module 164, with the bottom edge 352 resting on the flange 230 of the heater plate 176. With the oven enclosure 166 so disposed, the oven enclosure 166 cooperates with the heater plate 176 to define an oven space, within which the GC module 164 is disposed. The oven enclosure 166 is removably secured to the heater plate 176 by a bayonet type connection formed by the engagement of the bearings 232 of the heater plate 176 with the groove in the interior surface of the side wall 348 of the oven enclosure 166. The oven enclosure 166 helps conduct heat from the heater plate 176 around the column assembly 182 to provide a more even temperature distribution within the column assembly 182 and to help isolate the column assembly 182 from the ambient temperature conditions. A heating element may be secured to the oven enclosure 166 to further improve the temperature distribution and thermal isolation of the column assembly 182.

Dewar

Figure 10:
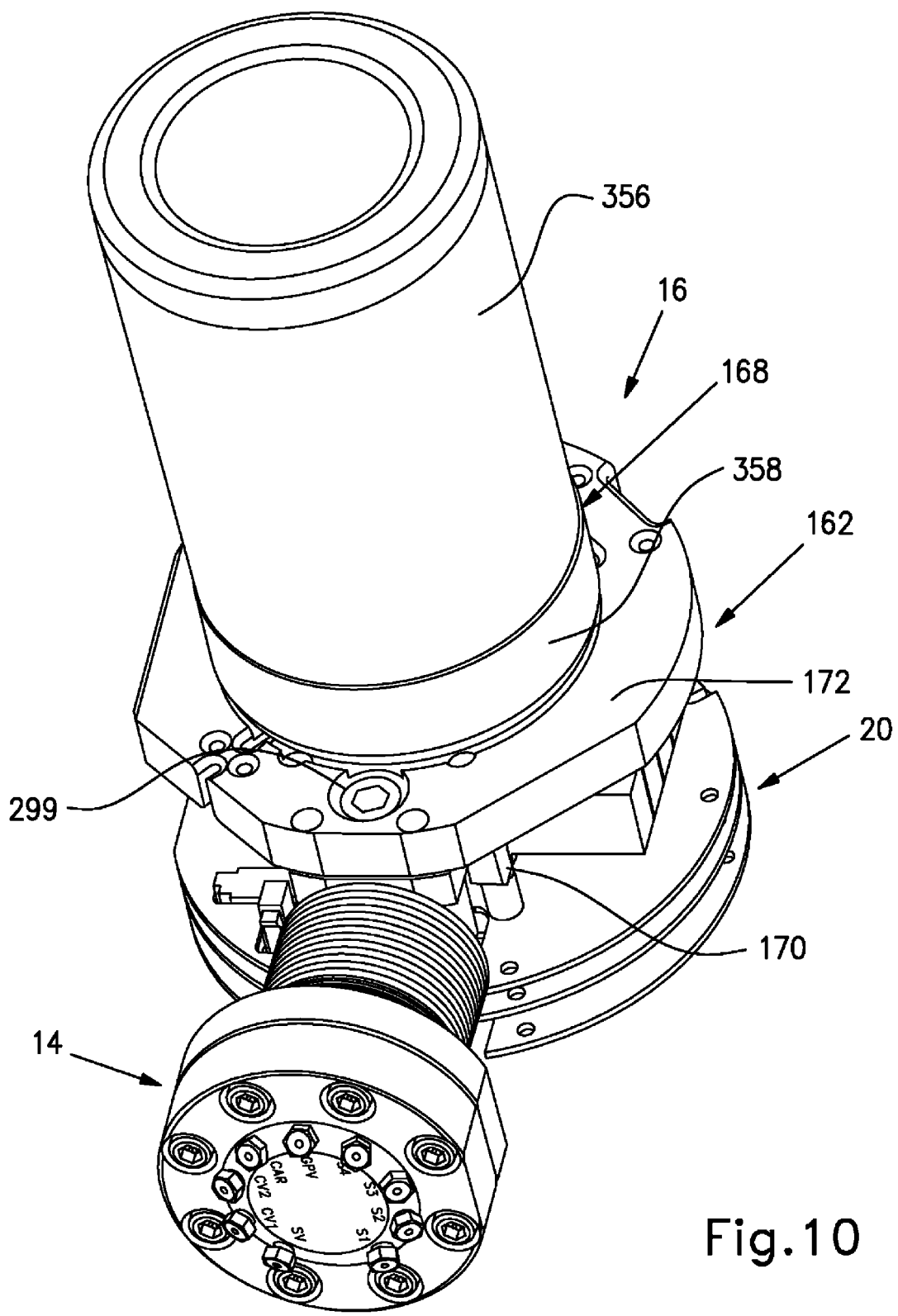
FIG. 10 shows a perspective view of the feed-through module secured to an analytical module of the gas chromatograph.

Referring back to FIGS. 10 and 11, the dewar 356 is cylindrical in shape and has a hollow interior and a closed outer end. An inner portion of the dewar 356 has a narrowed diameter, thereby forming a neck. The neck includes an exterior thread and an annular rim that defines an enlarged opening through which the interior may be accessed. The dewar 356 includes an inner shell nested within an outer shell so as form a narrow space therebetween. The inner and outer shells are sealed together at the neck. The narrow space between the inner and outer shell is evacuated almost entirely of air to produce a vacuum that prevents conduction and convection of heat. An inner surface of the outer shell and an outer surface of the inner shell are reflective or have reflective coatings to prevent heat from being transmitted via radiation. The inner and outer shells may be formed from stainless steel or other metal.

The dewar 356 is disposed over the oven enclosure 166, with the neck threadably secured to the cap 358 and the interior wall 364 of the cap 358 disposed inside the opening in the dewar 356. With the dewar 356 so disposed, the oven enclosure 166, the GC module 164, the heater plate 176 and the spacer 174 are disposed within the interior of the dewar 356, which provides an isolated environment in which the temperature of the oven space and thus the column assembly 182 can be closely regulated.

Analytical Processor Assembly

Figure 28:
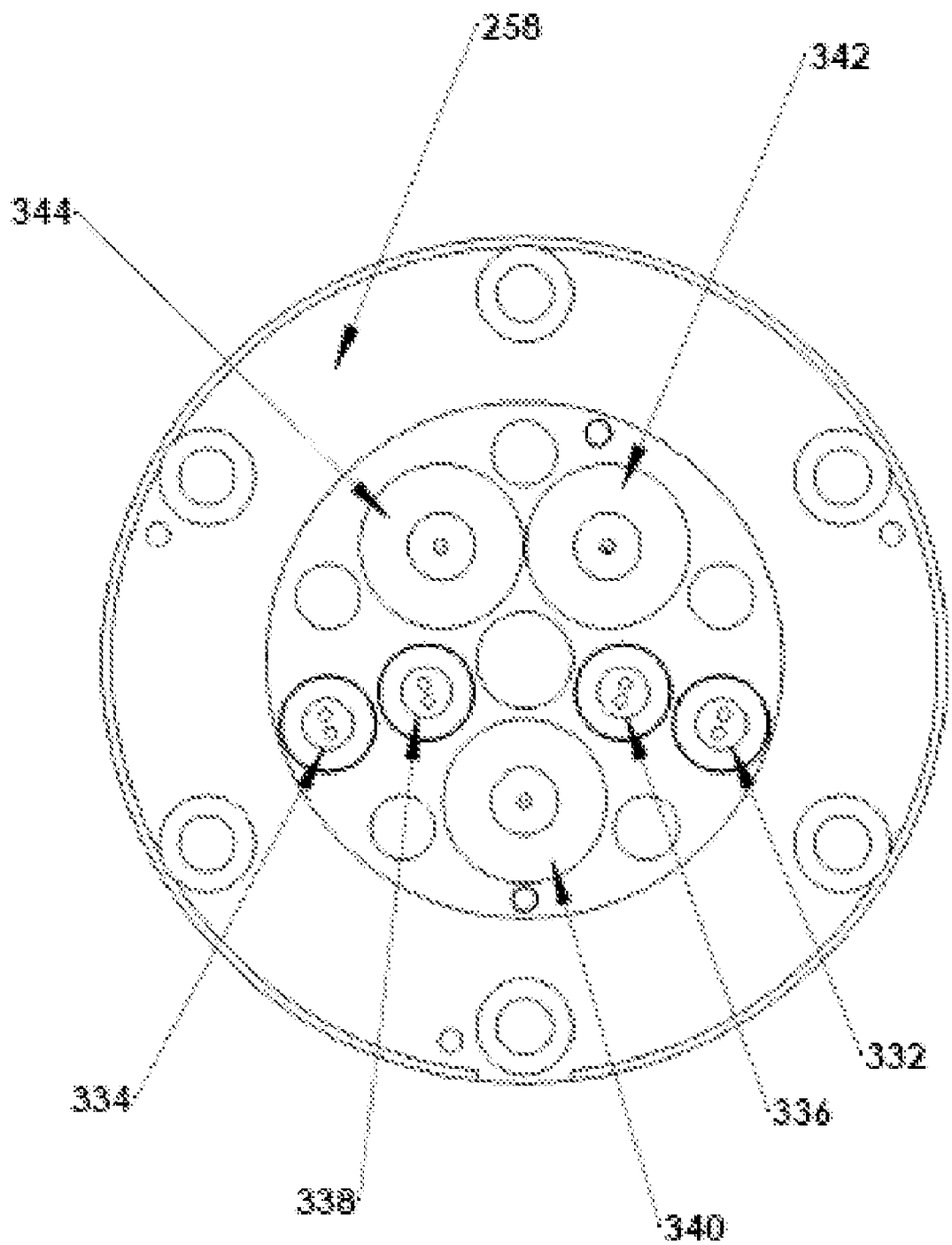
FIG. 28 shows a top plan view of a detector plate of the valve assembly of the GC module.
Figure 29:
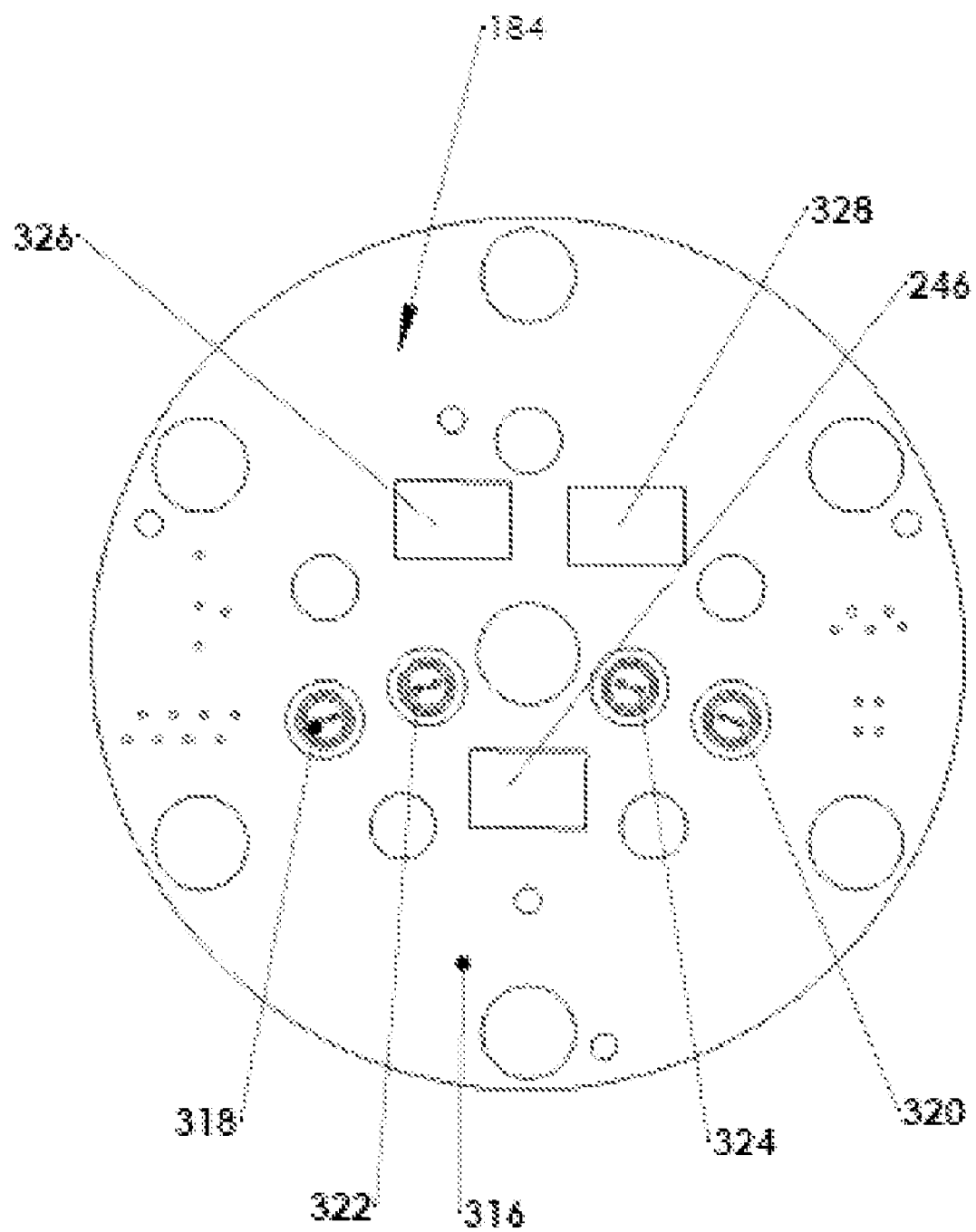
FIG. 29 shows a bottom plan view of a printed circuit board assembly mounted to the detector plate.
Figure 32:
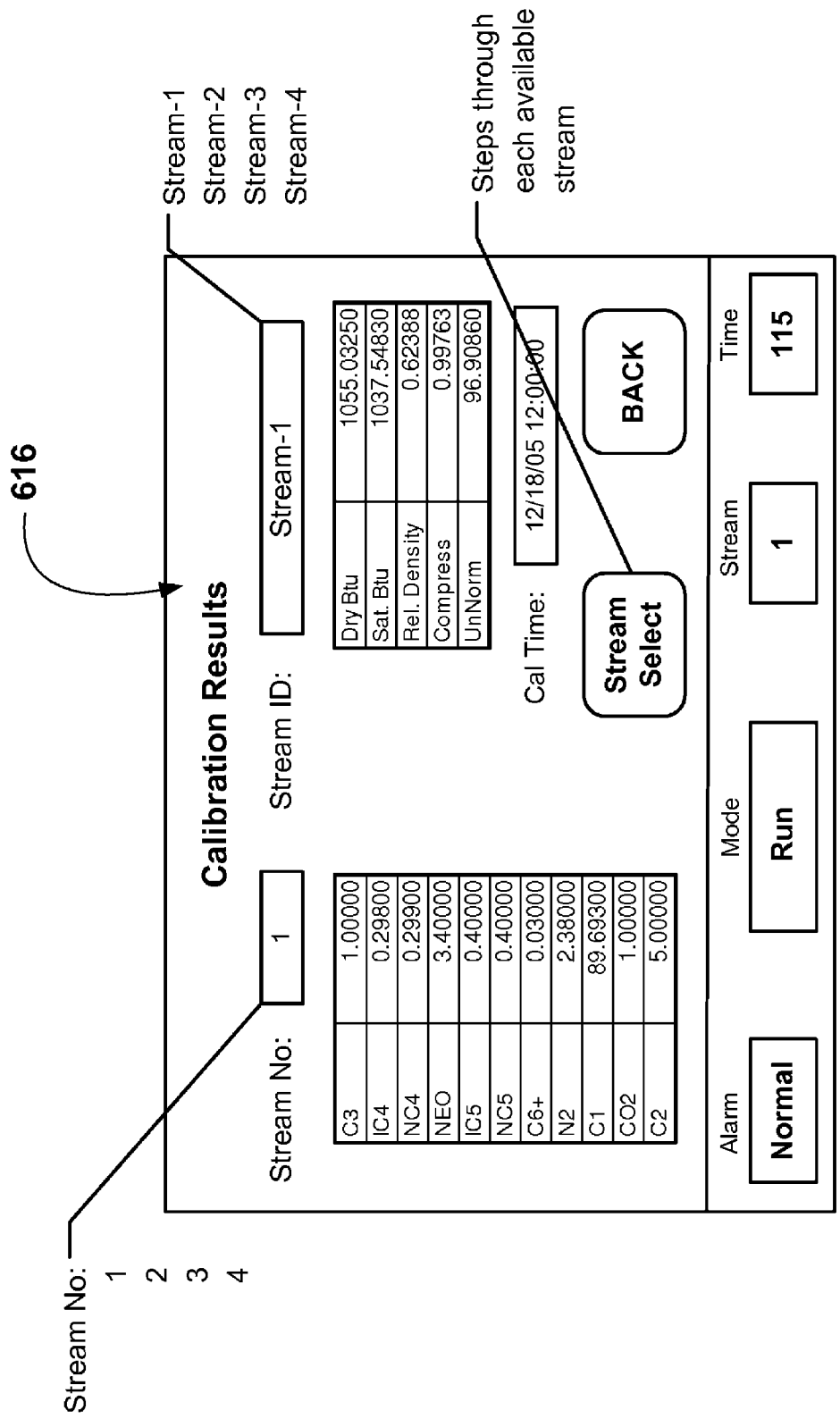
FIG. 32 shows a Calibration Results window of the GUI.

Referring now to FIGS. 28-30, the analytical processor assembly 20 includes an analytical PCA 160 secured between first and second mounting plates 398, 400. The analytical PCA 160 and the first and second mounting plates 398, 400 are secured together and to the secondary manifold plate 172 by a plurality of threaded bolts 402 fitted with nuts. Each of the bolts 402 extend through four spacers 404, two of which are disposed between the secondary manifold plate 172 and the first mounting plate 398, another one of which is disposed between the first manifold plate 398 and the analytical PCA 160, and still another one of which is disposed between the analytical PCA 160 and the second mounting plate 400. In this manner, the secondary manifold plate 172, the analytical PCA 160 and the first and second mounting plates 398, 400 are spaced apart from each other.

The analytical PCA 160 comprises a digital processor 408, which is designed for digital signal processing in real time. As used herein, the term "real time" means responding to stimuli within a bounded period of time. In an exemplary embodiment of the present invention, the digital processor 408 is a Blackfin® embedded processor available from Analog Devices and more particularly, a Blackfin® ADSP-BF533 embedded processor. The digital processor 408 provides fully digital based control of the flow control devices 210 and the cartridge heaters 150, 234 and can operate independently of the main CPU 24. The digital control provided by the digital processor 408 provides opportunities for performance enhancements and feature additions without adding hardware. The digital processor 408 communicates with memory 410, which may be serial flash memory having 1 MB storage space. The memory 410 stores all software algorithms run by the digital processor 408 to control the flow control devices 210 and the cartridge heaters 150, 234. In addition, the memory 410 stores a start-up program (or boot program) for the digital processor 408 that runs independently of the start-up program for the main CPU 24. Upon power-up of the gas chromatograph 10, the start-up program for the digital processor 408 interfaces with the memory 315 in the GC PCBA 184 to establish initial values for the process variables of the analytical module 16. More specifically, the start-up program: (1.) controls the cartridge heater 234 to set the temperature of the oven space to an initial value, which is retrieved from the memory 315; (2.) controls the cartridge heater 150 to set the temperature of the feed-through module 14 to an initial value, which is retrieved from the memory 315; (3.) controls the first and second pressure regulator valves 218, 220 to set the pressures of the carrier gas streams being fed to the first and second GC valves 188, 190 to initial values, which are retrieved from the memory 315; and (4) sets the pilot valve 216 so as to place the first and second GC valves 188, 190 in the "backflush" mode. Once the initial values for the process variables of the analytical module 16 are established by the start-up program, the digital processor 408 is ready to receive instructions from the main CPU 24 to run specific chromatographic analysis cycles.

The analytical PCA 160 has a serial communications interface with galvanic isolation. The serial interface can operate at up to 232 Kbaud for development and in-house testing purposes. In addition, the serial interface can be coupled to a personal computer (PC) for diagnostics via an external hardware level translator. The PC is provided with software that allows real-time observation of high speed, high resolution data from any of the on-board systems. A temperature sensor is mounted to the circuit board.

The provision of the digital processor 408 separate from the CPU 372 (i.e., as a separate, stand-alone microprocessor) permits the digital processor 408 to process input signals from sensors and detectors and generate control output signals to the flow control devices 210 and the cartridge heaters 150, 234 without having to handle highly non-deterministic events, such as communications with other devices external to the gas chromatograph 10 and user inputs from the GUI, or having to run other software algorithms. This dedication of the digital processor 408 permits the digital processor 408 to process the input signals and generate the control output signals in a faster and more consistent manner. It also allows for software changes and enhancements the main CPU 24 without affecting those functions requiring real-time processing.

Connection to Feed-Through Module

The analytical module 16 is secured to the feed-through module 14 (and, thus, the housing 12) by a single bolt 299 that extends through the aligned main mounting holes 196, 198 in the primary and secondary manifold plates 170, 172 and is threadably received in a threaded bore in a connection structure of the feed-through module 14. The bolt 299 has a hexagonal recess for receiving the end of a hexagonal driver, which is part of a tool kit provided with the gas chromatograph 10. The hexagonal driver has an elongated body so that the hexagonal driver can reach the bolt through the front access opening of the main section 22 of the housing 12.

Figure 8:
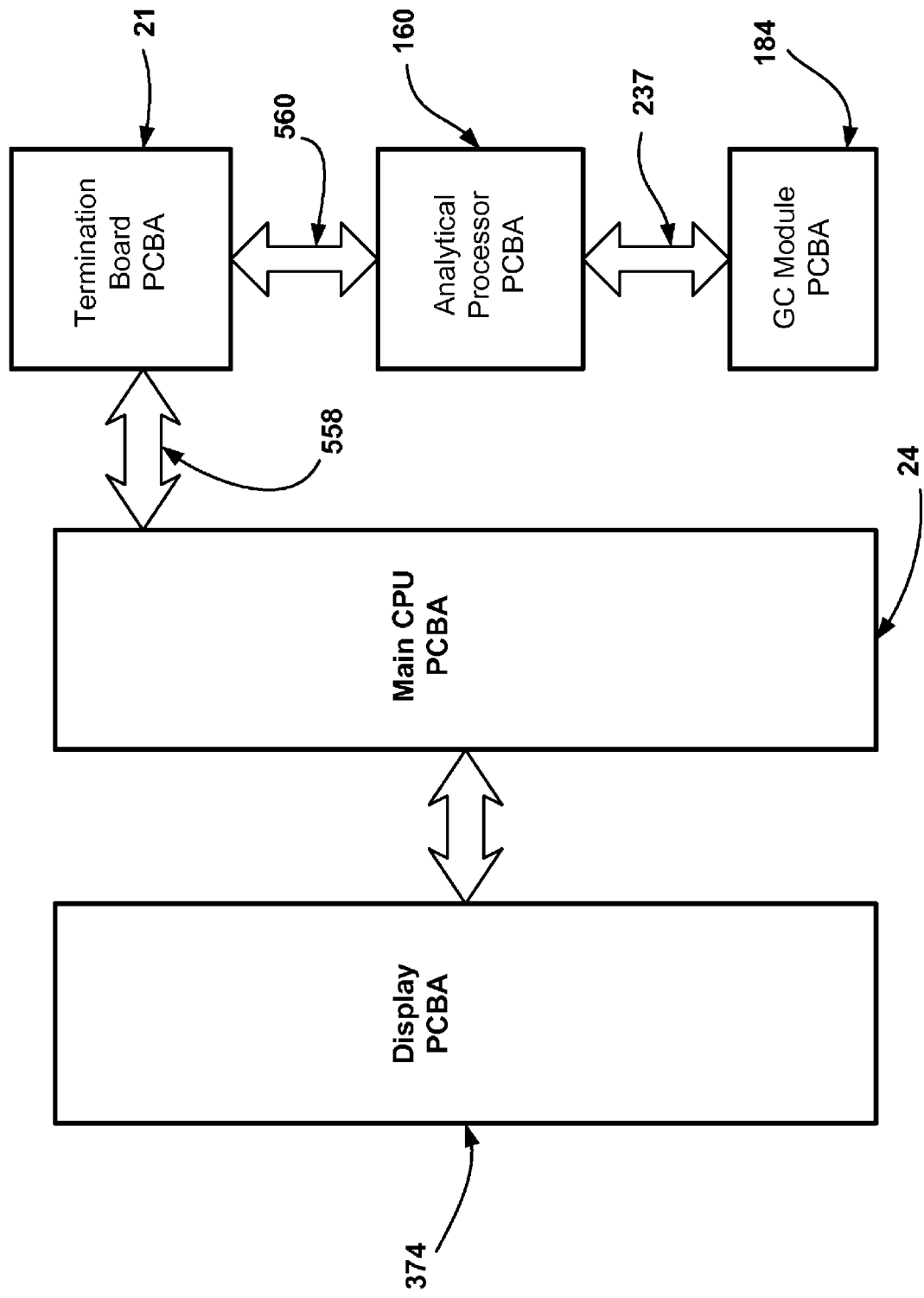
FIG. 8 shows a schematic drawing of the interconnection of an analytical processor printed circuit assembly, a main CPU, a termination assembly and a display printed circuit assembly.
Figure 9:
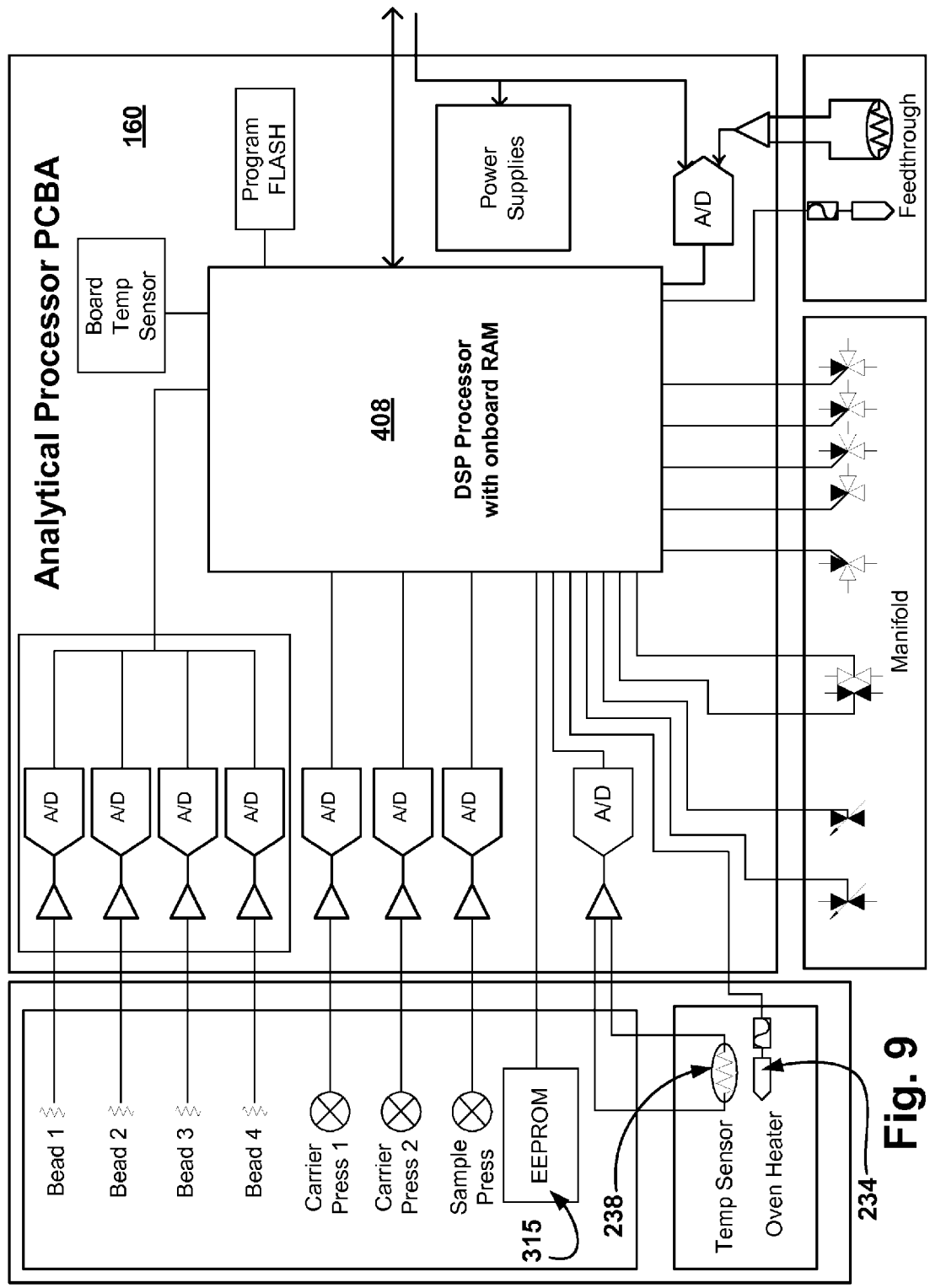
FIG. 9 shows a schematic drawing of the analytical processor printed circuit assembly.

As shown in FIG. 8, the main CPU 24 communicates with the analytical PCA 160 through the termination assembly 21. More specifically, the main CPU 24 is connected by a ribbon cable 558 (shown schematically in FIG. 8) to a first cable connector on the termination assembly 21, and the analytical PCA 160 is connected by a cable 560 (shown schematically in FIG. 8) to a second cable connector on the termination assembly 21. Communication from the main CPU 24 to the analytical PCA 160 travels through the ribbon cable 558 to the first cable connector of the terminal assembly 21, through the PCB 524 to the second cable connector and then through the cable to the analytical PCA 160. Communication from the analytical PCA 160 to the main CPU 24 occurs over the same path, but in the opposite direction. The GC PCBA 184 communicates with the analytical PCA 160 over the ribbon cable 237 that extends through the channel 236 in the heater plate 176.

III. Main Electronics Assembly

Referring now to FIGS. 8, 9, 18 and 19, the main electronics assembly 18 comprises the main CPU 24, a display PCA 374, a mounting plate 376, a mounting ring 378 and an outer bezel 382 with an enlarged opening.

The main CPU 24 handles system-level initialization, configuration, user interface, user command execution, connectivity functions, and overall system control of the electronics for the gas chromatograph 10. The main CPU 24 comprises a microprocessor mounted to a printed circuit board. The microprocessor may be an X86-type microprocessor, a RISC microprocessor (such as an ARM, DEC Alpha, PA-RISC, SPARC, MIPS, or PowerPC), or any other microprocessor suitable for use in a compact portable electronic device. In an exemplary embodiment, the microprocessor comprises a RISC core, which may be an ARM core, more particularly a 16/32-bit ARM9 core, still more particularly a 16/32-bit ARM920T core. The RISC core has a 16-bit Thumb instruction set, a 32-bit AMBA bus interface, a 5-stage integer pipeline, an 8-entry write buffer, separate 16 KB Instruction and 16 KB Data Caches and an MMU, which handles virtual memory management and is capable of supporting Windows® CE. An ARM9 core (including the ARM920T) is a 16/32 RISC processor designed by Advanced RISC Machines, Ltd. The RISC core is integrated with a set of common system peripherals, which includes a card interface for a secure digital (SD) flash memory card or a multimedia card, an LCD controller, an external memory controller, a multi-channel universal serial asynchronous receiver transmitter (USART), a watch dog timer, power management and USB host/device interface. An example of a commercially available microprocessor with a RISC core that may be used for the microprocessor is the S3C2410 microprocessor available from Samsung. An operating system, such as Windows® CE runs on the microprocessor. A memory system is connected to the microprocessor and includes volatile memory, such as a read-write memory (RAM) and a non-volatile memory such as boot read only memory (ROM). The non-volatile memory stores a start-up program (or boot program) for the microprocessor of the main CPU 24.

The main CPU 24 may also include an embedded TCP/IP stack and an HTTP web-server. In addition, the main CPU 24 may include a common gateway interface (CGI) module for communicating web page content to and from applications running in the main CPU 24 and the digital processor 408.

An SD socket is mounted to the printed circuit board of the main CPU and communicates with the card interface of the microprocessor. The SD socket holds an SD flash memory card. The SD flash memory card is small (measuring only 32 mm by 24 mm by 2.1 mm) and has a large amount of memory (such as 16 MB) that can store data from the operation of the gas chromatograph 10. The SD flash memory card may be removed from the gas chromatograph 10 and easily transported to another location where the stored data from the gas chromatograph 10 may be retrieved. A lithium battery 380 is connected to the main CPU 24 for providing backup power thereto.

The display PCA 374 includes a circular printed circuit board (PCB) 383 mounted behind the outer bezel 382. A VGA LCD display screen 384 is mounted to an outer side of the PCB 383 such that the display screen 384 is visible through the opening in the outer bezel 382. An infrared port 388 and a plurality of backlight LEDs 390 are mounted to the outer side of the PCB 383. The infrared port 388 is aligned with an opening in the outer bezel 382 and is operable to transmit and receive data via near infrared light waves (850-900 nm) in accordance with the Infrared Data Association (IrDA) standard and communicates with the microprocessor through the USART. When the display PCA 374 is mounted in the housing 12, behind the shield panel 96, the display screen 384 is positioned so as to be viewable through the shield panel 96 and the infrared port 388 is positioned so as to be able receive and transmit infrared signals through the shield panel 96.

Figure 19:
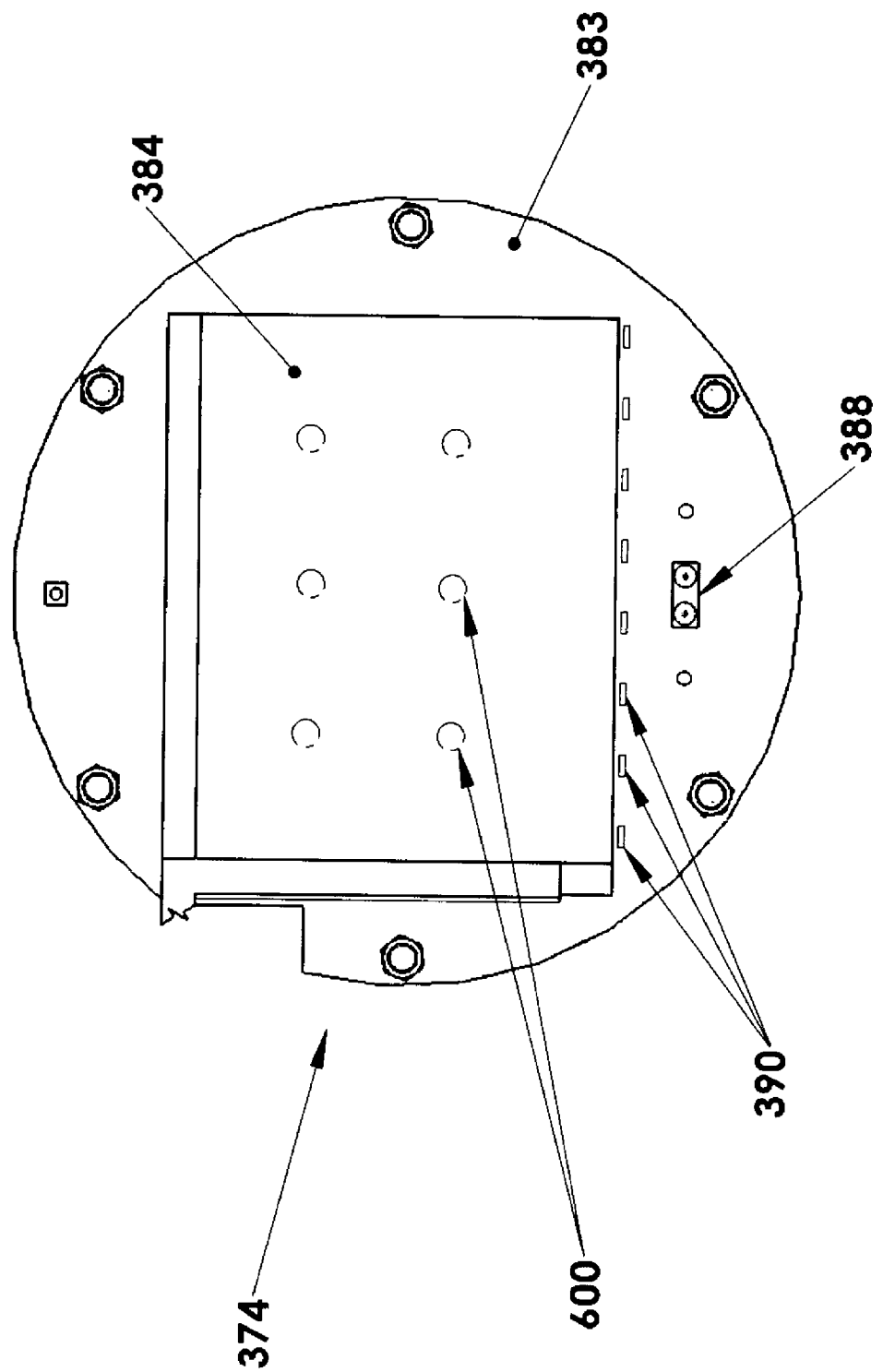
FIG. 19 shows a front plan view of an outer side of the display printed circuit assembly.

As shown in FIG. 19, a plurality of Hall-effect switches 600 are mounted to an inner side of the PCB 383 of the display PCA 374. Thus, the Hall-effect switches 600 are mounted behind the LCD display screen 384 and are separated from the LCD display screen 384 by the PCB 383 of the PCA 374. The number of Hall-effect switches 600 is limited and is substantially less than the number of liquid crystal cells forming the LCD display screen 384. The Hall-effect switches 600 are arranged in a pattern, such as a rectangle or a line, and are connected to the main CPU 24. As shown in FIG. 19, six Hall-effect switches 600 may be arranged in a rectangular pattern having a center that is aligned with the center of the LCD display screen 384. Each Hall-effect 600 switch may be a monolithic silicon chip that includes a Hall-effect element (HEE) coupled to a differential amplifier, which, in turn is coupled to a Schmitt-trigger threshold detector with built-in hysteresis. When a magnetic field is applied to the HEE, the HEE generates a Hall effect voltage, which is applied to the differential amplifier. The differential amplifier produces an output signal proportional to the Hall effect voltage. When the output signal from the differential amplifier is above a predetermined magnitude, the Schmitt-trigger threshold detector produces a digital "ON" signal, which is transmitted to the main CPU 24. Each of the Hall-effect switches 600 may be configured to activate, i.e., produce an "ON" signal when the Hall-effect switch 600 is disposed in a positive magnetic field. Alternately, each of the Hall-effect switches 600 may be configured to activate when the Hall-effect switch 600 is disposed in either a positive magnetic field or a negative magnetic field. As will be described more fully below, the Hall-effect switches 600 are used to navigate through a graphical user interface (GUI) of the gas chromatograph 10.

The display PCA 374, the main CPU 24 and the mounting plate 376 are secured together by a plurality of threaded bolts 392 fitted with nuts. Each of the bolts 392 extend through a pair of spacers 394, one of which is disposed between the display PCA 374 and the main CPU 24 and the other of which is disposed between the main CPU 24 and the mounting plate 376. In this manner, the display PCA 374, the main CPU 24 and the mounting plate 376 are spaced apart from each other. The mounting plate 376 is secured by a plurality of legs 396 to the mounting ring 378, which comprises a stainless steel hose clamp. The main electronics assembly 18 is mounted on the dewar 356 by disposing the mounting ring 378 over the dewar 356 such that the mounting plate 376 rests on the outer end of the dewar 356. A clamping mechanism of the mounting ring 378 is then adjusted to clamp the mounting ring 378 to the dewar 356.

IV. Communication with the GC

Figure 20:
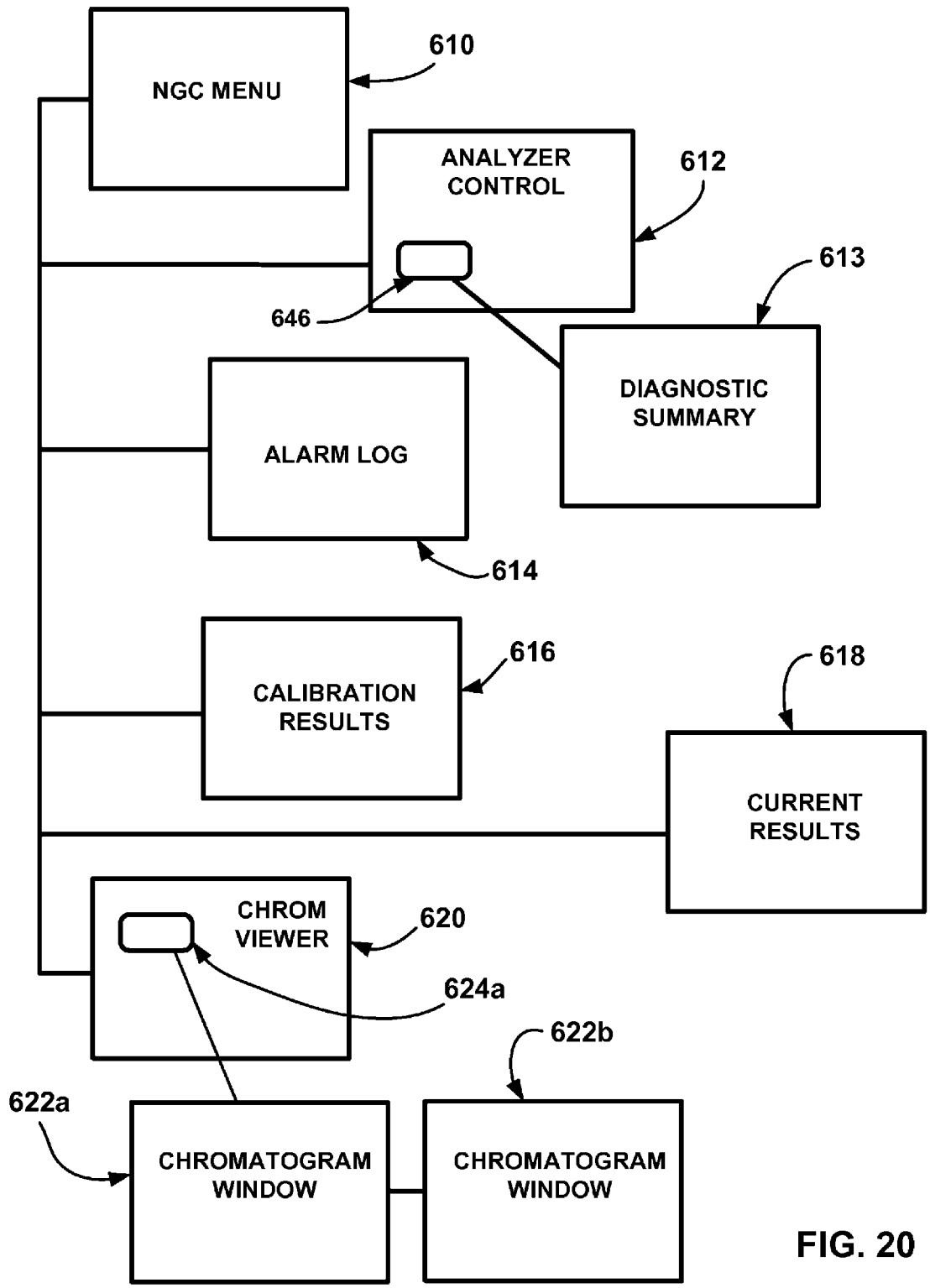
FIG. 20 shows windows of a graphical user interface (GUI) of the gas chromatograph.
Figure 21:
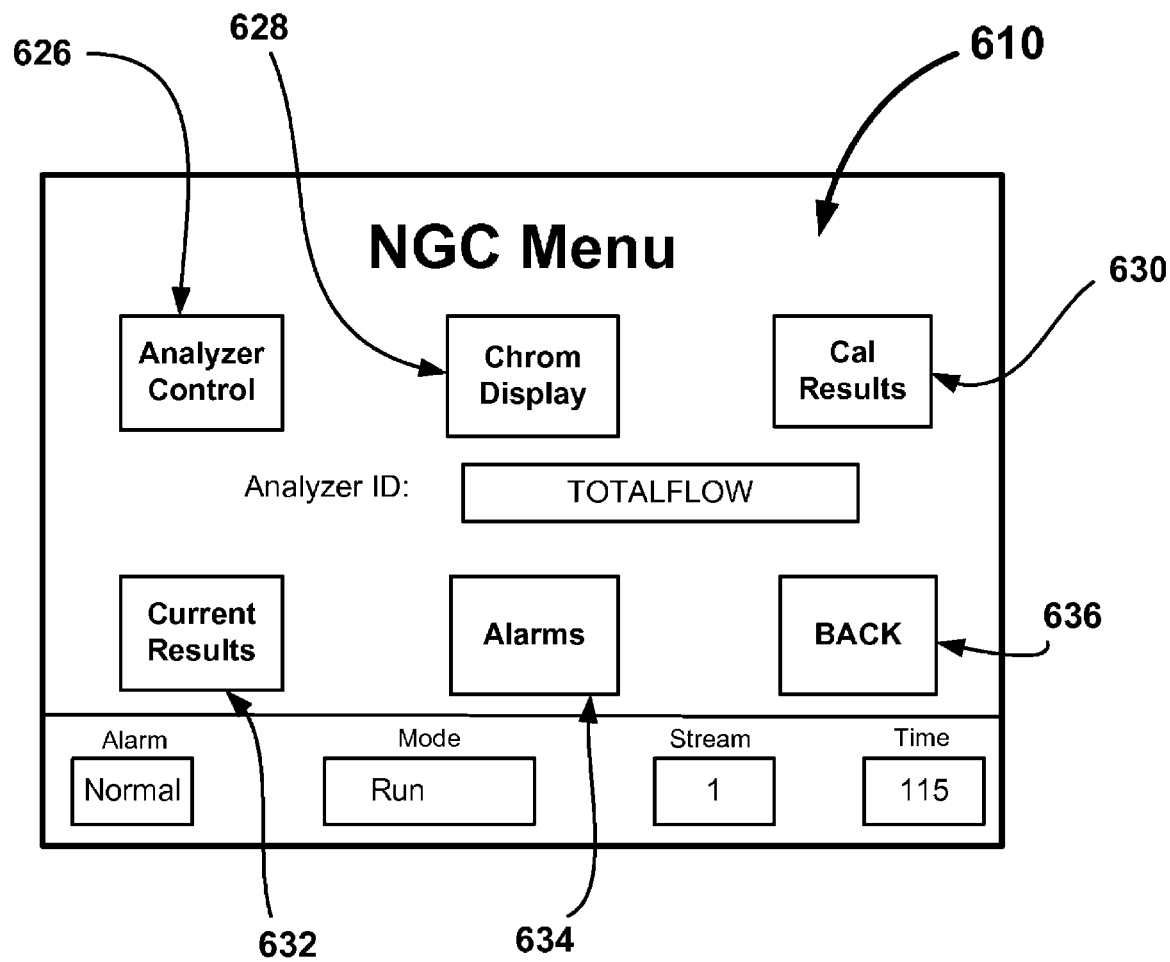
FIG. 21 shows an NGC Menu window of the GUI.
Figure 22:
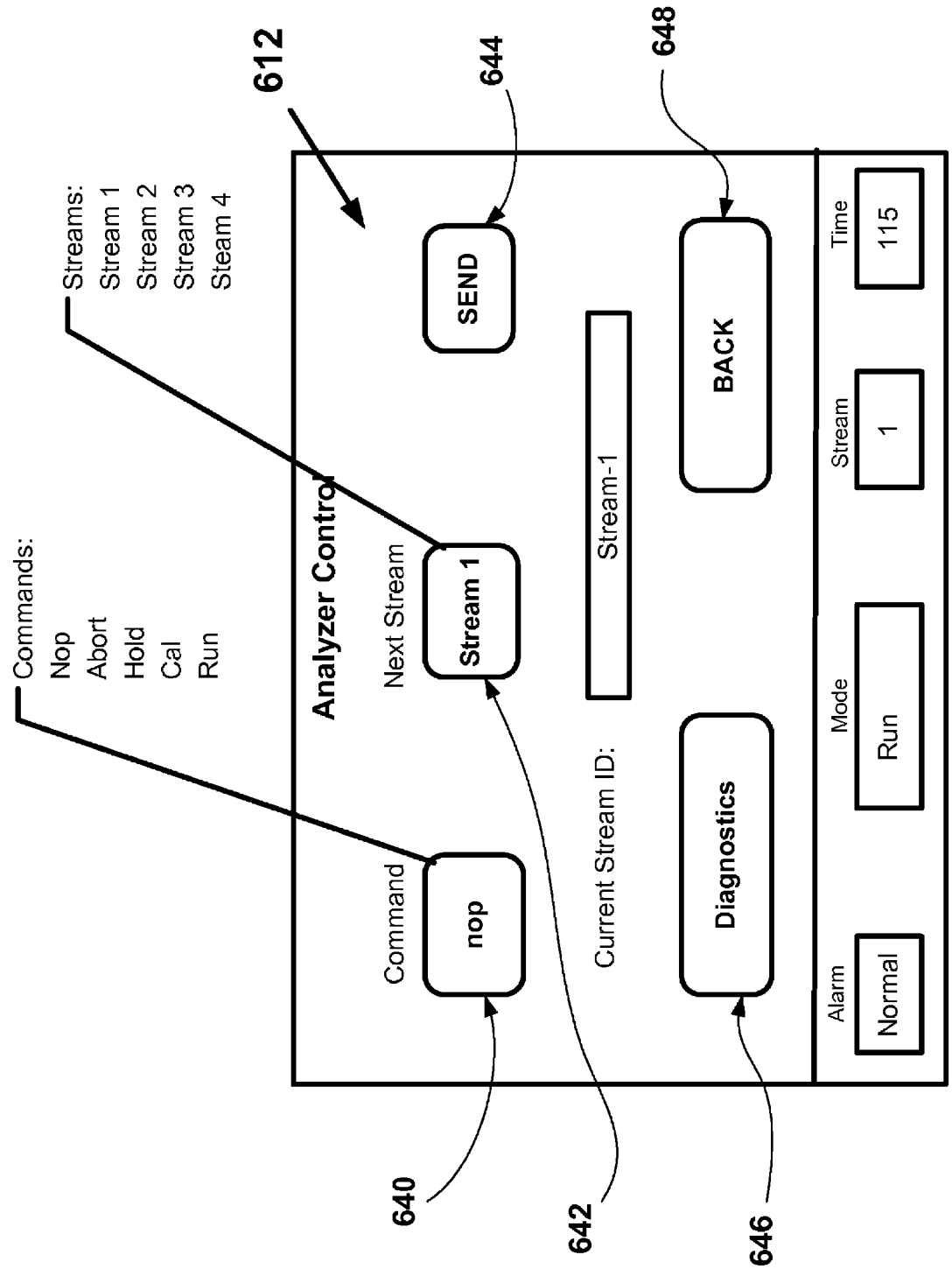
FIG. 22 shows an Analyzer Control window of the GUI.

The operating system running on the main CPU 24 supports the GUI, which allows a user to view and control the operation of the gas chromatograph 10. Referring now to FIGS. 20, 21 and 22, the GUI includes a plurality of windows that are displayable on the LCD display screen 384. The windows, which are generated and controlled by a GUI software application stored in memory and running on the main CPU 24, include an NGC Menu window 610, an Analyzer Control window 612, a Diagnostic Summary window 613, an Alarm Log window 614, a Calibration Results window 616, a Current Results window 618, a Chromatograph Viewer window 620, and chromatogram windows 622. Navigation through the windows and selection of options presented therein are accomplished using the Hall-effect switches 600 and a stylus (not shown) containing a magnet.

The NGC Menu window 610 includes six selection button icons, namely an Analyzer Control button 626, a Chrom Display button 628, a Cal Results button 630, a Current Results button 632, an Alarms button 634 and a Back button 636. The six buttons 626-636 are aligned with the six Hall-effect switches 600 that are disposed behind the LCD display window 384, respectively. Actuation of one of the buttons 626-634 will cause the window associated with the actuated button to be displayed on the LCD display window 384 in lieu of the NGC Menu window 610. For example, actuation of the Analyzer Control button 626 will cause the Analyzer Control window 612 to be displayed on the LCD display screen 384, selection of the Chrom Display button 628 will cause the Chromatograph Viewer window 620 to be displayed on the LCD display screen 384, and so on. A desired button is "actuated" by placing the stylus against or in close proximity to the shield panel 96 and in alignment with the desired button. This placement of the stylus activates the Hall-effect switch 600 aligned with the desired button. The "On" signal generated by the activated Hall-effect switch 600 is input to the GUI software application, which then causes the LCD display screen 384 to display the window associated with the selected button. The "actuation" of other buttons in other windows is performed in the same manner (i.e., with the stylus) and pursuant to the same operating mechanism (i.e., magnetically activating an aligned Hall-effect switch 660).

As set forth above, the Analyzer Control window 612 is accessed from the NGC Menu window 61. The Analyzer Control window 612 includes five selection button icons, namely a Command button 640, a Stream button 642, a Send button 644, a Diagnostics button 646 and a Back button 648. These five buttons are aligned with five of the six Hall-effect switches 600. The Command button 640 and the Stream button 642 are each operated in a scrolling manner to select an option. For example, the Stream button 642 is used to select one of four options, namely Stream 1, Stream 2, Stream 3, or Stream 4. When the Analyzer Control window 612 is being displayed on the LCD display screen 384, a first actuation of the Stream button 642 (i.e., activation (with the stylus) of the Hall-effect switch 600 aligned with the Stream button 642) causes the GUI software application to display Stream 1 in the Stream button 642 (as shown). In other words, Stream 1 is provisionally selected. After the Hall-effect switch 600 is deactivated by moving the stylus away from the LCD display screen 384, a second actuation of the Stream button 642 causes the GUI software application to display "Stream 2" in the Stream button 642, i.e., Stream 2 is provisionally selected. In the same manner, a third actuation provisionally selects Stream 3, a fourth actuation provisionally selects Stream 4, a fifth actuation provisionally selects Stream 1 again, and so on. Similar to the Stream button 642, the Command button 640 is actuated in a scrolling manner to display one of five commands in the Command button 604, i.e., to provisionally select one of five commands. These commands are: "Nop", "Abort", "Hold", "Cal" and "Run".

Once a user has provisionally selected a stream (e.g. Stream 1) and a command (e.g. Run), the user actuates the Send button 644 (i.e., activates the Hall-effect switch 600 aligned with the Send button 644), which causes the GUI software application to command the digital processor 408 to perform an analysis of the composition of Stream 1. In response, the digital processor 408, inter alia, actuates the sample valve 212a for Stream 1 to feed the gas of Stream 1 to the first and second sample loops 288, 290, and then, after a predetermined period of time, places the first and second GC valves 188, 190 into the "inject mode".

Actuation of the Diagnostics button 646 in the Analyzer Control window 612 causes the GUI software application to display the Diagnostic Summary window 613, which, inter alia, displays the pressures in the first and second columns 282, 286 and the temperature in the oven space. Actuation of the Back button 648 causes the GUI software application to go back and again display the NGC Menu window 610.

Figure 33:
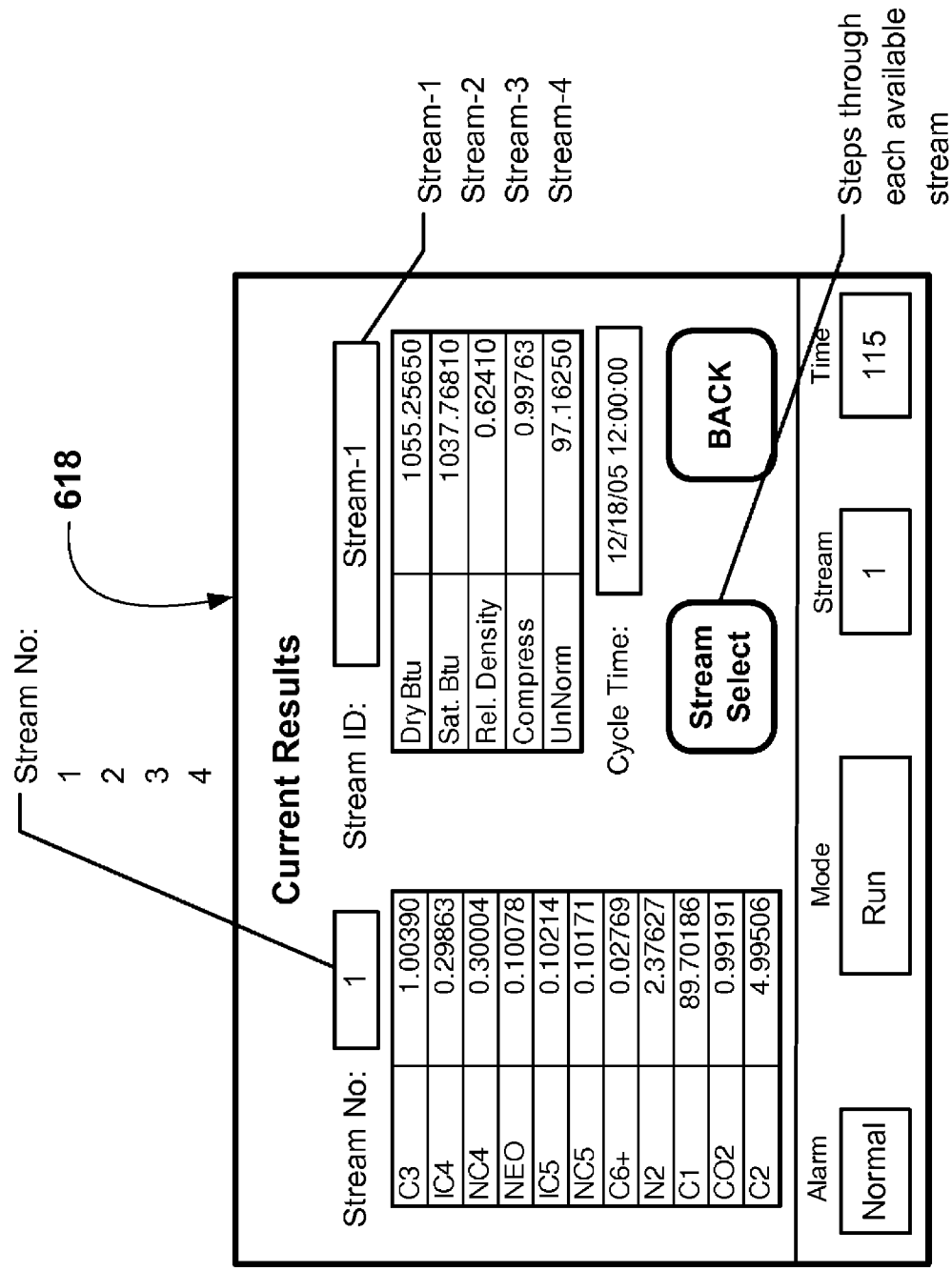
FIG. 33 shows a Current Results window of the GUI.
Figure 34:
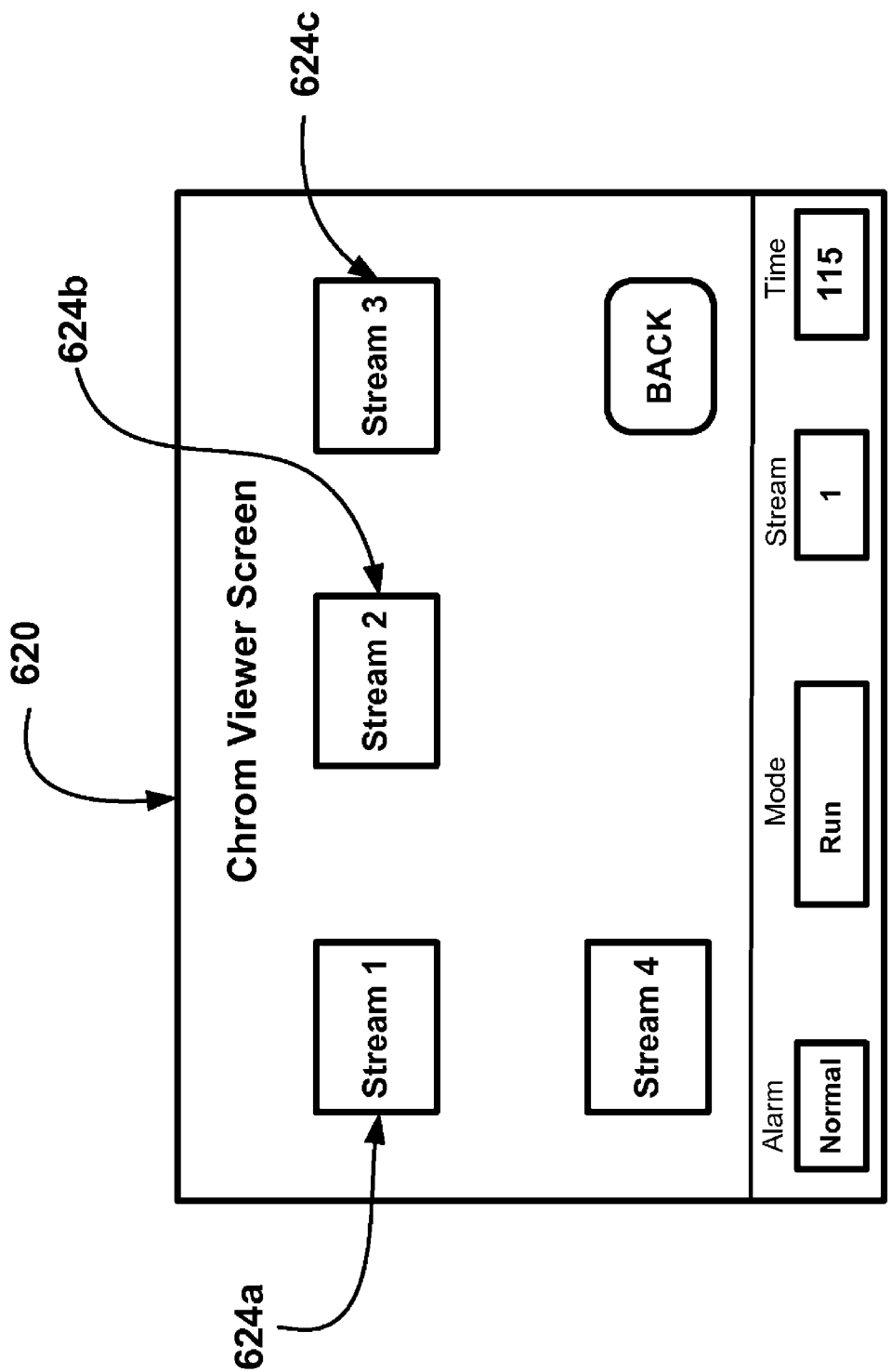
FIG. 34 shows a Chrom Viewer Screen.
Figure 35:
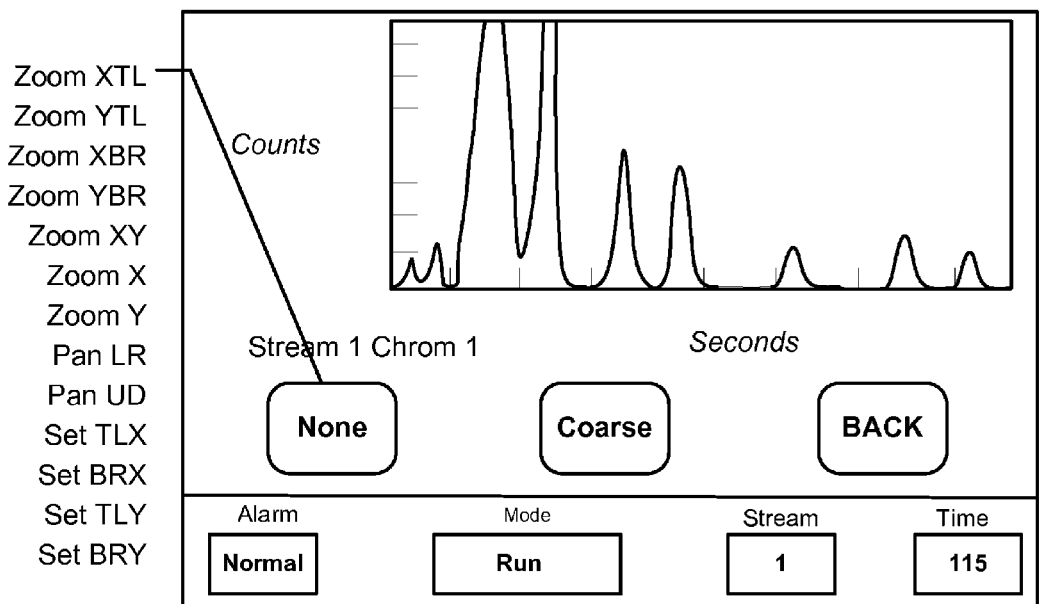
FIG. 35 shows a first chromatogram window of the GUI.
Figure 36:
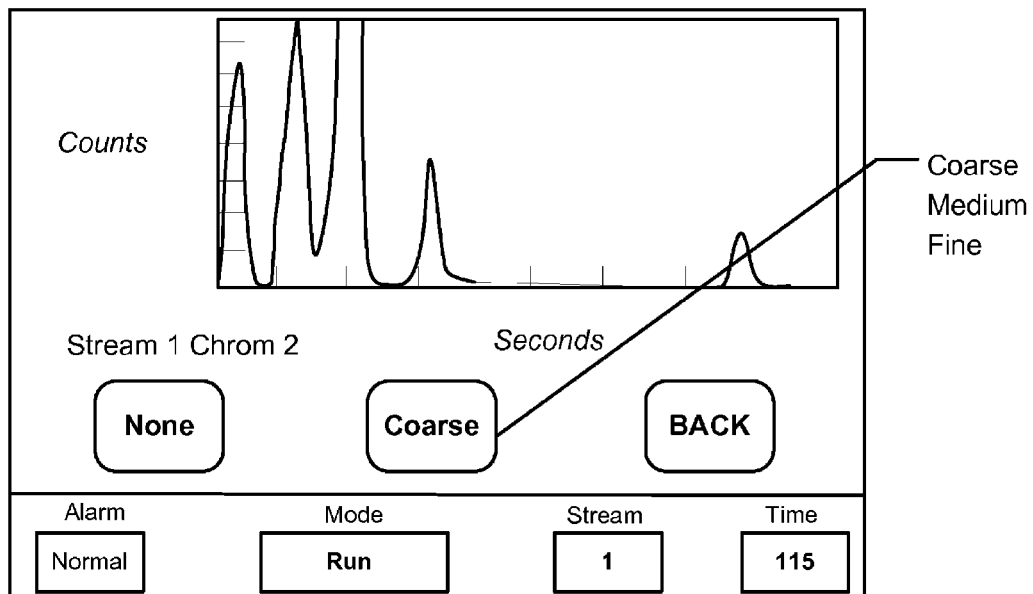
FIG. 36 shows a second chromatogram window of the GUI.

From the NGC Menu window 610, a user can also access the Current Results window 618 by actuating the Current Results button 630 and can access the Chrom Viewer window 620 (shown in FIG. 34) by actuating the Chrom Display button 628. The Chrom Results window 618 (shown in FIG. 33) displays the composition of a selected gas stream in a tabular format. The Chrom Viewer window 620 provides access to the chromatogram windows 622a and 622b (shown in FIGS. 35 and 36) through stream buttons 624a, b, c. The chromatogram windows 622a,b display chromatograms for the gases of Streams 1, 2, 3 and 4, respectively. In this regard, it should be noted that a chromatogram is a plot of the output signal of a detector (e.g. TCD 320 or TCD 324) versus time and shows the Gaussian peaks for the various gas components, as is described more fully below.

In addition to communicating with the gas chromatograph 10 through the GUI, a user at the site where the gas chromatograph 10 is installed may communicate with the gas chromatograph 10 through a mobile interface device (such as a laptop computer, or personal digital assistant) having a USB port, a Bluetooth transceiver and/or an infrared port. If the mobile device is equipped with a USB port, the mobile device may communicate with the gas chromatograph 10 over a cable connected to the communication port 88 of the gas chromatograph 10. If the mobile device is equipped with a Bluetooth transceiver, the mobile device may communicate with the gas chromatograph 10 via radio signals transmitted between the mobile device and the antenna 74 and the wireless transceiver in the gas chromatograph 10. If the mobile device is equipped with an infrared port, the mobile device may communicate with the gas chromatograph 110 via infrared light transmitted between the mobile device and the infrared port 388 of the gas chromatograph 110. It should be noted that if communication port 88 is in use, i.e., connected to another device, the infrared port 388 is made inactive.

Communication with the gas chromatograph 10 from a remote location may also be accomplished using a serial line connected to one of a plurality of serial ports in the termination assembly 21. The gas chromatograph 10 may also be connected through an Ethernet port in the termination assembly 21 to a local area network (LAN), a wide area network (WAN), or the Internet. Web pages similar, if not identical to the windows 610-622 in the GUI, may be generated by the web server in the main CPU 24 and transmitted over the Internet to a user at a remote location.

V. GC Features and Operation

It should be appreciated from the foregoing description that the gas chromatograph 10 has a modular construction that permits the gas chromatograph 10 to be quickly and easily disassembled and reassembled. This is advantageous because it permits the GC module 164 to be facilely replaced with another GC module that is constructed to analyze a gas different than the gas analyzed by the GC module 164. In this manner, the gas chromatograph 10 can be modified to analyze many different types of gases.

Each replacement GC module has substantially the same construction as the GC module 164, except for the columns 280-286. Each replacement GC module has columns that are specifically constructed for measuring a particular gas.

A GC module 164 may be swapped with a replacement GC module 164 while the analytical module 16 remains disposed in the housing 12 and secured to the feed-through module 14, or the GC module 164 may be swapped with a replacement GC module 164 after the entire analytical module 16 has been unfastened from the feed-through module 14 and removed from the housing 12. Either way, the front access cover 28 is unthreaded from the front collar 34 and removed. The clamping mechanism of the mounting ring 378 is then loosened and the main electronics assembly 18 is removed from the dewar 356. If the entire analytical module 16 is being removed, the bolt 299 is removed using the hexagonal driver and the analytical module 16 is pulled through the front access opening in the main section 22 of the housing 12. The dewar 356 is unthreaded from the cap 358 and removed, thereby exposing the oven enclosure 166. The oven enclosure 166 is then removed from engagement with the heater plate 176 by pulling the oven enclosure 166 away from the heater plate 176 and the rest of the manifold module 162. With the oven enclosure 166 so removed, the GC module 164 is now exposed. The ribbon cable 237 is first disconnected from the GC PCBA 184 and then the GC module 164 is rotated counter-clockwise to unthread the bolt 270 from the heater plate 176. After the GC module 164 is unthreaded and removed, the replacement GC module is then mounted to the manifold module 162 by threading its bolt 270 into the central bore 240 of the heater plate 17 and connecting the ribbon cable 237 to the replacement GC module. The oven enclosure 166 and the dewar 356 are then reinstalled. If the entire analytical module 16 was removed from the housing 12, the analytical module 16 is reinserted into the main section 22 through the front access opening thereof and secured to the feed-through module 14 with the bolt 299. The main electronics assembly 18 and the front access cover 28 are then reinstalled.

As with the GC module 164, each replacement GC module contains a memory 315 that stores calibration and other characterization data for the replacement GC module. The storage of calibration and other characterization data in the memories 315 of the GC module 164 and the replacement GC module, respectively, as opposed to other more centralized memory, such as the memory 410 for the digital processor 408, permits the GC module 164 to be swapped with the replacement GC module without having to reprogram memory, which greatly simplifies the replacement process.

Figure 23:
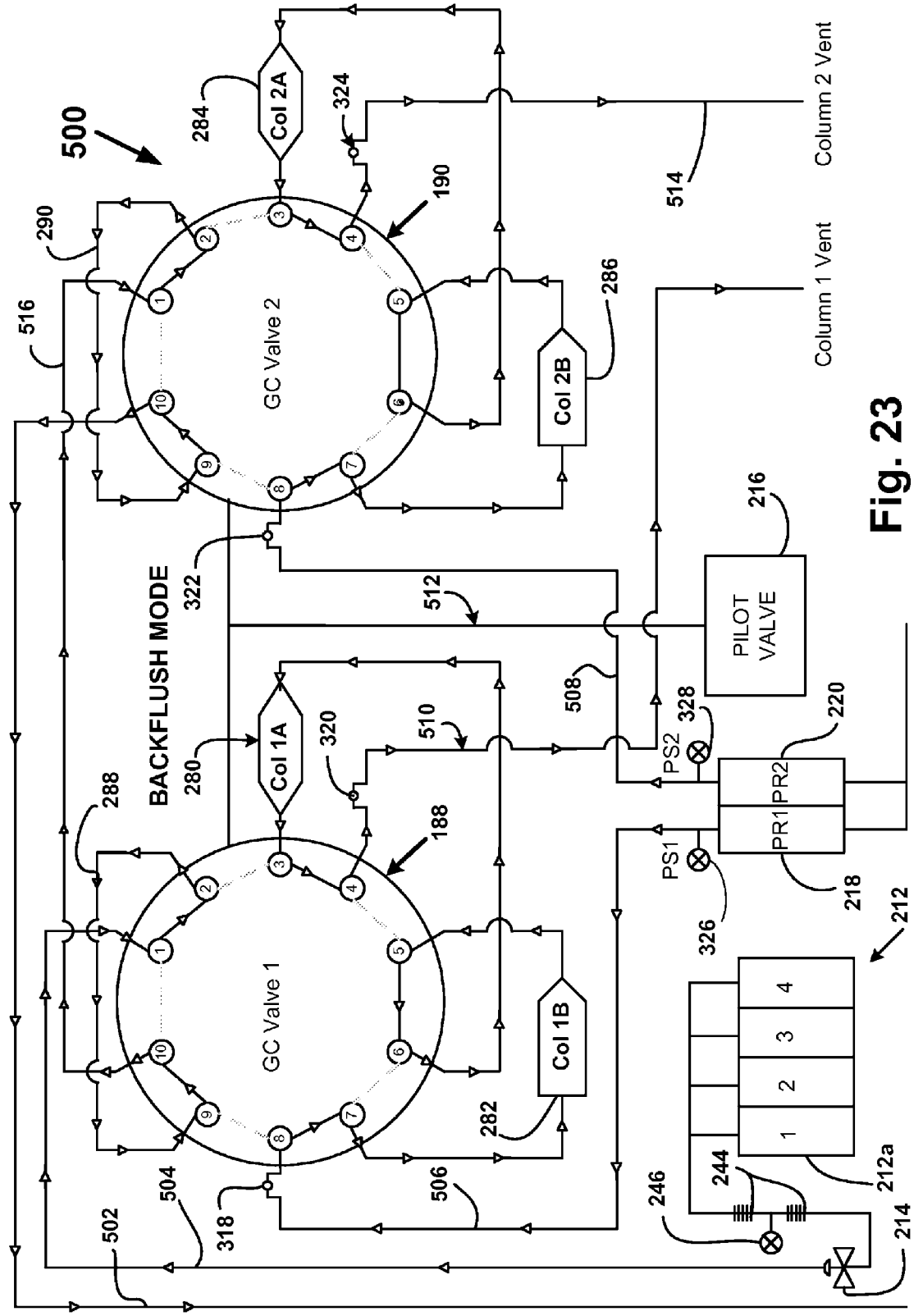
FIG. 23 shows a schematic diagram of the flow paths of sample gas and carrier gas through the gas chromatograph when the valve assembly is in a "backflush mode"
Figure 24:
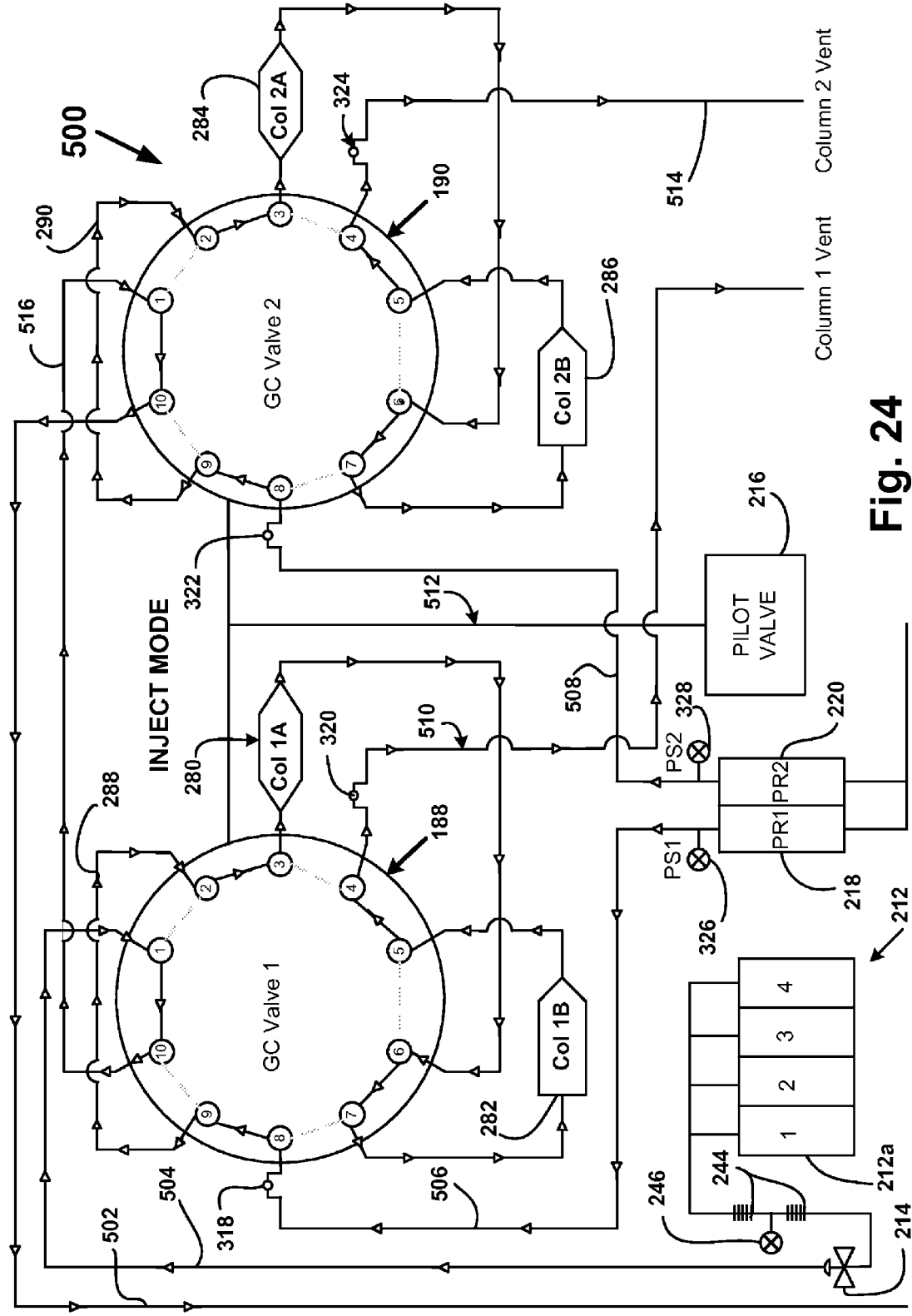
FIG. 24 shows a schematic diagram of the flow paths of sample gas and carrier gas through the gas chromatograph when the valve assembly is in an "inject mode"

Referring now to FIGS. 23 and 24, there are shown schematics of flow paths of sample gas and carrier gas through the gas chromatograph 10. More specifically, FIGS. 23 and 24 show schematics of a GC flow circuit 500 that comprises the inlet and vent paths through the feed-through module 14 and the first through sixth internal passage networks in the primary manifold plate 170, the secondary manifold plate 172, the spacer 174, the heater plate 176, the valve assembly 180 and the spool 278, respectively. The GC flow circuit 500 is, inter alia, represented by lines 502, 504, 506, 508, 510, 512, 514 and is interconnected with the electrical flow devices 210 and the first and second GC valves 188, 190. As set forth above, the first and second GC valves 188, 190 each have ports 1-10 and are movable between a "backflush" mode and an "inject" mode. Line 502 connects port 10 of the second GC valve 190 to the sample vent. Line 504 connects port 1 of the first GC valve 188, through the shut-off valve 214, to a selected one of the sample inputs. Line 506 connects port 8 of the first GC valve 188, through the first pressure regulator valve 218, to the carrier gas input. Line 508 connects port 8 of the second GC valve 190, through the second pressure regulator valve 220, to the carrier gas input. Line 510 connects port 4 of the first GC valve 188 to column vent 1. Line 512 connects the first and second GC valves 188, 190, through the pilot valve 216, to the carrier gas input. Line 514 connects port 4 of the second GC valve 190 to the column 2 vent. Line 516 connects port 10 of the first GC valve 188 to port 1 of the second GC valve 190.

When the first and second GC valves 188, 190 are in the "backflush" mode, as shown in FIG. 23, a stream of sample gas flows from a selected one of the sample inputs through line 504 to port 1 to port 2 of the first GC valve 188, through the first sample loop 288 and thence to port 9 to port 10 of the first GC valve 188. From port 10 of the first GC valve 188, the stream of sample gas flows through line 516 to port 1 to port 2 of the second GC valve 190, through the second sample loop 290 and thence to port 9 to port 10 of the second GC valve 190. The stream of sample gas then flows through line 502 to the sample vent. Thus, while the first and second GC valves 188, 190 are in the "backflush" mode, the first and second sample loops 288, 290 are filled with first and second gas samples, respectively. If the first and second GC valves 188, 190 are then moved to the "inject" mode, the first and second gas samples are trapped within the first and second sample loops 288, 290.

When the first and second GC valves 188, 190 are in the "inject" mode (as shown in FIG. 24), the carrier gas flows through lines 506, 508 and the first and second reference TCDs 318, 322 to the ports 8 of the first and second GC valves 188, 190. In the first GC valve 188, the carrier gas flows to port 9 and into the first sample loop 288, and in the second GC valve 190, the carrier gas flows to port 9 and into the second sample loop 290. The carrier gas entering the first and second sample loops 288, 290 forces the first and second gas samples trapped therein to exit the first and second sample loops 288, 290 through ports 2 of the first and second GC valves 188, 190, respectively. The first gas sample travels to port 3 of the first GC valve 188, then passes through the first preliminary column 280 to port 6 to port 7 of the first GC valve 188, then passes through the first column 282, travels to port 5 and exits the first GC valve 188 through port 4. Similarly, the second gas sample travels to port 3 of the second GC valve 190, then passes through the second preliminary column 284 to port 6 to port 7 of the second GC valve 190, then passes through the second column 286, travels to port 5 and exits the first GC valve 188 through port 4. After respectively exiting the first and second GC valves 188, 190, the first and second gas samples feed into the first and second sensor TCDs 320, 324, respectively, where the gas samples are analyzed, as will be described further below. The first and second gas samples then travel to the column 1 and column 2 vents through lines 510, 514, respectively.

After the first and second gas samples have been analyzed and the first and second GC valves 188, 190 are moved back to the "backflush" mode, carrier gas backflushes the first, second, third and fourth TCDs 318-324, the first and second preliminary columns 280, 284 and the first and second columns 282, 286 to remove remnants of the first and second gas samples. With regard to the first GC valve 188, the backflush travel path of the carrier gas is the first TCD 318, port 8, port 7, the first column 282, port 5, port 6, the first preliminary column 280, port 3, port 4, the second TCD 320 and then through line 510 to the column 1 vent. With regard to the second GC valve 190, the backflush travel path of the carrier gas is the third TCD 322, port 8, port 7, the second column 286, port 5, port 6, the second preliminary column 284, port 3, port 4, the fourth TCD 324 and then through line 514 to the column 2 vent.

As described above, the GC module 164 (which includes the TCDs 318-324 and the first and second GC valves 188, 190 and associated flow paths) receives a single stream of sample gas, divides the stream into a pair of gas samples and analyzes the gas samples in parallel. Such parallel analysis is faster than conventional serial analysis. It should be appreciated that the analysis speed can be increased further by utilizing additional GC valves and TCDs so as to analyze three or more samples in parallel.

For ease of description, only the analysis of the first gas sample will be discussed, it being understood that the analysis of the second gas sample is substantially the same. As the first gas sample travels through the columns 280, 282 the components of the first gas sample separate from one another by virtue of differences in their rates of interaction (absorption and de-absorption) with the adsorbents in the columns 280, 282. The different components are therefore retained in the columns 280, 282 for different lengths of time and arrive at the second TCD 320 (sense detector) at different, characteristic times. The design of the columns 280, 282, their operating conditions, such as temperature, and gas flow, are optimized and carefully controlled so as to provide good and consistent separation between the components.

For repeatable quantification of gas components, the temperature of the TCDs 318-324, the columns 280-286, the first and second sample loops 288, 290 and the first and second GC valves 188, 190 are closely regulated to maintain a constant temperature. This close regulation is facilitated by integrating the foregoing components into the GC module 164, mounting the GC module 164 on the heater plate 176, and enclosing both the GC module 164 and the heater plate 176 in the thermally insulating dewar 356, which is supported on the thermally insulating spacer 174. The heater plate 176 is heated by the cartridge heater 234. The temperature of the heater plate 176 is sensed by the oven temperature sensor 238, which is an NTC thermistor-type temperature sensor. The oven temperature sensor 238 generates a temperature signal which is transmitted to input circuitry in the analytical PCA 160, which conditions and digitizes the signal and then passes the signal to the digital processor 408. Using the digitized temperature signal from the oven temperature sensor 238, the digital processor 408 determines the correct control response for heating the GC module 164 and then outputs a pulse-width modulated control signal to a power transistor which then sources current to the cartridge heater 234. The digital processor 408 uses a software-implemented PID (Proportional-Integral-Derivative)-type control algorithm stored in the memory 410 to generate the control signal that controls the cartridge heater 234 and, thus, the temperature of the oven space. By having the temperature control algorithm performed in software, information about the temperature control process can be provided to the main CPU 24. Such information may include the oven power being used, which can provide valuable diagnostic information.

In addition to the temperature of the GC module 164, the pressure of the carrier gas is closely controlled. This is significant because even very small changes in gas pressure cause changes in gas density, which, in turn changes the thermal conductivity of the carrier, thereby resulting in a deflection in the output signal of the first reference TCD 318. Very small changes in the carrier gas pressure also causes pressure changes across the first GC valve 188, the columns 280, 282, etc., which also results in a deflection in the output signal of the first sensor TCD 320, as well as changes in the retention times of the Gaussian peaks, which affects measurement repeatability.

The first and second carrier pressure sensors 326, 328 generate pressure signals which are transmitted to input circuitry in the analytical PCA 160, which conditions and digitizes the signals and then passes the signals to the digital processor 408. Since the first and second carrier gas pressure sensors 326, 328 are located on the GC PCBA 184 in the thermally stable oven space defined by the oven enclosure 166 and the heater plate 176, the first and second carrier gas pressure sensors 326, 328 do not need to be temperature compensated. Using the digitized pressure signals from the first and second carrier pressure sensors 326, 328, the digital processor 408 determines the correct control response for providing carrier gas to the first and second GC valves 188, 190 and then outputs pulse-width modulated control signals to power transistors which then source currents to the first and second pressure regulating valves 218, 220. The digital processor 408 uses a software-implemented PID (Proportional-Integral-Derivative)-type control algorithm to generate the control signals that control the first and second pressure regulating valves 218, 220. By having the pressure control algorithm performed in software, information about the pressure control process can be provided to the main CPU 24. This information includes valuable diagnostic information about the control signals driving the first and second pressure regulating valves 218, 220, as well as the error term being computed within the software. Such information provides a measure of the effort being expended to control the first and second pressure regulating valves 218, 220, which, in turn can be used to determine if a leak exists in the GC flow circuit 500 by watching the trend of this control variable at the level of the Main CPU 24.

It should be noted that the analytical PCA 160 utilizes pulse width modulation (PWM) drive for all the flow control devices 210. This permits 12V devices to be utilized with 24V system voltages because the digital processor 408 can dynamically change the average current being sourced to each device based on the instantaneous system voltage that it also measures. This feature also achieves a significant reduction in the power being dissipated by the devices under normal operation by using pick and hold current drive methods, often reducing the instantaneous power consumed by the devices by up to 75%, thereby reducing overall system power requirements, and making the gas chromatograph 10 more suitable for low power operation.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. An analyzer for measuring one or more process variables, the analyzer comprising:
a housing adapted for field mounting;
a display screen visible from the exterior of the housing;
a magnetically-actuated switch mounted behind the display screen;
an electronics assembly disposed in the housing and including a microprocessor and memory, the microprocessor being connected to the display screen and the magnetically-actuated switch; and
a graphical user interface (GUI) software application stored in the memory and executable by the microprocessor to display a plurality of windows on the display screen, the windows comprising first and second windows, the first window containing a navigation icon that is associated with the second window and is aligned with the switch, wherein when the first window is displayed and the switch aligned with the navigation icon is activated, the GUI software application displays the second window.

2. The analyzer of claim 1, wherein the switch is a Hall-effect switch.

3. The analyzer of claim 1, wherein the analyzer comprises a plurality of magnetically-actuated switches and the second window contains one or more graphical selection icons, each selection icon being aligned with one of the switches and being associated with a plurality of different analyzer operational parameters, wherein the number of times the aligned switch is activated determines the analyzer operational parameter that is selected.

4. The analyzer of claim 3, wherein for each selection icon, the name of a selected operational parameter is displayed in the selection icon.

5. The analyzer of claim 3, wherein the selection icons in the second window comprise a process variable selection icon associated with a plurality of different process variables and a command selection icon associated with a plurality of different commands.

6. The analyzer of claim 5, wherein the second window further comprises a graphical send icon associated with one of the switches, wherein when one of the process variables and one of the commands have been selected and the switch associated with the send icon is activated, the analyzer performs the selected command with regard to the selected process variable.

7. The analyzer of claim 1, wherein the electronics assembly further comprises a circuit board having first and second sides, and wherein the display screen is mounted to the first side of the circuit board and the switch is mounted to the second side of the circuit board.

8. The analyzer of claim 7, further comprising a transparent panel mounted to the housing, and wherein the display screen is mounted inward of the panel and is visible through the panel.

9. The analyzer of claim 8, wherein the panel comprises at least one sheet of glass or transparent plastic coated with at least one transparent conductive coating.

10. The analyzer of claim 1, further comprising an analytical assembly mounted inside the housing, the analytical assembly being operable to measure the one or more process variables, and wherein the display screen is mounted inside the housing with the analytical assembly.

11. The analyzer of claim 10, wherein the housing of the analyzer is explosion-proof.

12. The analyzer of claim 11, wherein the analyzer is a gas chromatograph.

13. The analyzer of claim 12, wherein the analytical assembly comprises one or more columns for separating components of a fluid, and wherein the one or more process variables comprises the amount of the components of the fluid.

14. The analyzer of claim 1, wherein the first and second windows are not displayed concurrently on the display screen.

15. The analyzer of claim 1, wherein the navigation icon contains indicia identifying the second window.

16. The analyzer of claim 1, wherein the switch is actuated by placing a magnet proximate to the navigation icon.

17. The analyzer of claim 1, wherein the analyzer further comprises a magnetically-actuated second switch mounted behind the display screen and connected to the microprocessor;
  wherein the windows further comprise a third window;
  wherein the first window further contains a second navigation icon that is associated with the third window and is aligned with the second switch; and
  wherein when the first window is displayed and the second switch aligned with the second navigation icon is activated, the GUI software application displays the third window.

18. The analyzer of claim 1, wherein the analyzer comprises a plurality of magnetically-actuated switches;
  wherein the second window contains a back icon that is aligned with one of the switches; and
  wherein when the second window is displayed and the switch aligned with the back icon is activated, the GUI software application displays the first window again.

* * * * *